United States Patent
Xia

(10) Patent No.: US 7,205,004 B2
(45) Date of Patent: Apr. 17, 2007

(54) HERBAL COMPOSITION FOR TREATMENT OF NEURONAL INJURIES AND NEURONAL DEGENERATION, METHODS TO PREPARE THE SAME AND USES THEREOF

(76) Inventor: YongChao Xia, Provincial Hospital of Chinese Medicine, LanZhou 730050 GanSu Province (CN)

( * ) Notice: Subject to any disclaimer, the term of this patent is extended or adjusted under 35 U.S.C. 154(b) by 0 days.

(21) Appl. No.: 10/442,865

(22) Filed: May 22, 2003

(65) Prior Publication Data

US 2003/0211178 A1 Nov. 13, 2003

Related U.S. Application Data

(63) Continuation of application No. PCT/IB01/02859, filed on Nov. 21, 2001.

(60) Provisional application No. 60/253,013, filed on Nov. 22, 2000.

(51) Int. Cl.
 A61K 36/232 (2006.01)
 A61K 36/236 (2006.01)
 A61K 36/8969 (2006.01)
 A61K 36/481 (2006.01)
 A61K 36/484 (2006.01)

(52) U.S. Cl. ............... 424/725; 424/773; 424/520; 424/757

(58) Field of Classification Search ........... 424/725, 424/773, 520
See application file for complete search history.

(56) References Cited

OTHER PUBLICATIONS

Chinese Patent Application No. 96122265.4, May 27, 1998, YongChao Xia. "Bu-Nao-Gao".
Chinese Patent Application No. 99119227.3, Mar. 8, 2000, Zhan Shan Guo. "Medicinal Wine for treating hyperlipidemia and high blood-viscosity".
Chinese Patent Application No.93106328.0, May 11, 1994, Qishong Gao and Haifeng Suen "Method of preparation for Flaccidity Recovery".
"The Chinese Materia Medica", edited by Beijing University of Traditional Chinese Medicine, Jun. 1984, pp. 208-209, 211-212.
PCT International Preliminary Examination Report, Jun. 12, 2003 for Yongchao Xia, PCT/IB01/02859, "Herbal Composition For Treatment of Neuronal Injuries and Neuronal Degeneration, Methods to Prepare the Same and Uses Thereof."
PCT International Search Report Examination Report, Oct. 3, 2002, for YongChao Xia, PCT/IB01/02859, "Herbal Composition for Treatment of Neuronal Injuries and Neuronal Degeneration, Methods to Prepare the Same and Uses Thereof."
CN, A, 1182603, May 27, 1998, The Traditional Chinese Medical Hospital of Gansu.
CN, A, 1086430, May 11, 1994, GAO, Qishong.
CN, A, 1246368, Mar. 8, 2000, GUO, Zhanshan.

*Primary Examiner*—Susan Hoffman
(74) *Attorney, Agent, or Firm*—Law Offices of Albert Wai-Kit Chan, LLC

(57) ABSTRACT

This invention provides a composition of herbs comprising Radix *angelica sinensis* (DangGui) 15–60%, *Ligusticum chuanxiong* (ChuanXiong) 5–20%, Hirudo (ShuiZhi) 3–7%, *Polygonatum sibiricum* (HuangJing) 4–15%. This invention further provides various uses of this composition.

18 Claims, No Drawings

HERBAL COMPOSITION FOR TREATMENT OF NEURONAL INJURIES AND NEURONAL DEGENERATION, METHODS TO PREPARE THE SAME AND USES THEREOF

The application disclosed herein is a continuation application of International Application PCT/IB01/02859, filed Nov. 21, 2001, which claims priority of U.S. Ser. No. 60/253,013, filed Nov. 22, 2000, the contents of which are hereby incorporated by reference into this application.

Throughout this application, various references are referred to. Disclosures of these publications in their entireties are hereby incorporated by reference into this application to more fully describe the state of the art to which this invention pertains.

FIELD OF THE INVENTION

This invention covers a formulation of Chinese medicine (1). This invention also provides a method of its preparation. Finally, this invention provides for the various uses of this formulation.

BACKGROUND OF THE INVENTION

This formulation of Chinese Medicine has been temporarily named Bu-Nao-Gao (meaning a decoction for brain nourishment). This formulation was derived from the "finger citron powder (Fo-Shou) therapeutic serie of Chinese medicine" developed by the inventor (2, 3). This "finger citron powder (Fo-Shou) therapeutic serie was derived and modified based on an ancient formulation of Chinese medicine named "Finger citron powder" (also termed "Fo-Shou powder" or "XiongQui powder"). The ancient formulation of "Finger citron powder" contains two ingredients (Radix Angelica Sinensis and Ligusticum chuanxiong), and can be found in "TaiPingShengHuiFang" and also be described in the classical books of Chinese Medicine "PuJiFang" and "YiZongJinJian". This ancient formulation was mainly used for treating various prenatal and postpartum disorders. This "finger citron powder (Fo-Shou) therapeutic serie" developed by the inventor contains many formulations which differ in compositions, but all had an emphasis on the higher dosage use of Radix Angelica Sinensis from Min County, GanSu province, P. R. China.

During the early phase of this invention, the inventor explored many different strategies of Chinese Medicine for the treatment of neurological diseases. The early publications (4–29), though still an incomplete list, reflected some of the many attempts made by the inventor to define a therapeutic role (or a consensus formulation) for treating diseases/or disorders of this system. Disorders successfully treated and described in these early reports include (many are anecdotal cases): all kinds of paralysis resulting from head trauma, cranial nerve injuries, aphasia, motor neuron disease, sequel of apoplexy, pseudo-bulbar palsy of apoplexy, post-infective arachnoiditis, sequel of encephalitis, patient in vegetative state, myelitis, polyneuritis, muscle stiffness, muscle spasm, etc. In these publications (also these not listed here), many ingredients later described in this application were used at various time points and at various dosages, and ingredients not included in this application were also used. Nevertheless, no consensus formulation can be obviously derived from any of the previous reports. With accumulated clinical experience of using various decoctions and their combinations in treating various neurological diseases, a consensus formulation was eventually derived, and its efficacy for various uses became established.

Under normal circumstances, neurons within the brain or spinal cord are unable to regenerate damaged connections. As a result of this, neuronal injuries of all causes (i.e. spinal cord injury, head trauma, stroke or neurodegenerative diseases) generally lead to serious and irreversible loss in functions. The consequences of neuronal injuries and neurodegenerative diseases put a heavy burden on all of humanity. The following are examples describing the realities of the above diseases or conditions:

Feeblemindedness and cerebral palsy: According to the statistical data reported in America in 1973, the worldwide prevalence of feeblemindedness is 3% (mild type: 2.5%, moderate type: 0.5%); its prevalence in China is 0.5–2.7% (mild type) and 0.3–1% (severe type); the prevalence of cerebral palsy is 0.1–0.2% worldwide, and 0.1–0.4% (approximately 2 million in China). Our diagnosis of feeblemindedness also includes cerebral Palsy. According the most recent information released by American National Health Institute (NIH): more than 500,000 Americans have cerebral palsy (this information may also be considered as a reference for its global trend). The number of children and adults it affects has remained essentially unchanged or perhaps risen slightly over the past 30 years.

For paralysis or other disability caused by brain injury: There are currently 5.3 million Americans living with disability caused by brain injury. Each year, at least 1.5 million people sustain brain injury (at a speed one every 21 seconds). This public health concern ranks as the leading cause of death and disability in children and young adults. Currently, prevention is the only known cure for brain injury. This statistics came from the information released by the Brain Injury Association, Inc. (Alexandria, Va., USA). This information may also be used as a reference for the worldwide trend of brain injury.

Dementia of all types: e.g. Alzheimer's disease (AD), the most common cause of dementia among people age 65 and older. It was estimated that up to 4 million people in America currently suffer with the disease, and the prevalence (the number of people with the disease at any one time) doubles every 5 years beyond age 65. Approximately 360,000 new cases are estimated to emerge each year and to increase as the population ages (According to the 2000 progress report on Alzheimer's disease from the National Health Institute (NIH) of America).

Motor neuron disease: its most severe form-Amyotrophic lateral sclerosis (ALS), or Lou Gehrig's disease, is a devastating neurological disorder that robs people of their ability to move, eventually causing death. ALS is relentless in its progression. About 5,000 people in the United States develop ALS each year, and about 90% of them die within 5 years when symptoms are first detected. There is so far no proven means to stop or significantly slow the progress of ALS (according to the most recent information released by the National Health Institute (NIH) of America—updated May 18, 2000).

All above statistical data (although mainly derived from sources in America) can be used as a reference for the worldwide trend of each problem.

Treatment of all above conditions has been one of the biggest challenges to our biomedical field. Treatment regimes worldwide involve neuroprotectants and physical therapies, and these regimes have been expensive with only limited clinical benefits. No generally accepted effective treatment is so far available. In recent years, there has been some progress in using Chinese Medicine for the treatment of the above diseases; however, their effectiveness has been limited due to big case-to-case variations and low reproducibility.

SUMMARY OF THE INVENTION

This invention covers a formulation of Chinese Medicine.

It is the objective of this invention to provide a highly effective, economical and convenient treatment for neuronal injuries by all causes: e.g. children feeblemindedness and cerebral palsies, sequel after head injury and neurodegenerative diseases.

It is also an object of this invention to provide a method of its preparation to achieve its clinical efficacy.

DETAILED DESCRIPTION OF THE INVENTION

This invention is a combination of Chinese Medicine comprising the following components in the weight ratio indicated: Radix *angelica sinensis* (DangGui) 15–60%, *Ligusticum chuanxiong* (ChuanXiong) 5–20%, Hirudo (ShuiZhi) 3–7%, *Polygonatum sibiricum* (HuangJing) 4–15%.

In addition, as most other compositions of Chinese Medicine, *Glycyrrhiza uralensis* (Gancao) is routinely included in the composition at the weight ratio 1.5–3.5%.

This formulation may be altered for example in the following ways:

Alternation #1) The component *Ligusticum chuanxiong* (ChuanXiong) can be replaced by any of the following: *Carthamus timctorius* (Hong Hua) or *Prunus persica* (Tao Ren) or *Achyrantes bidentata* (Huai Nuxi) without changing its weight ratio in the formulation.

Alternation #2) The *Polygonatum sibiricum* (HuangJing) can be supplemented by any (or any combinations) of the following ingredients in the weight ratio indicated: *Lycium chinense* mill (GouQiZi) 3–5%, *Curculigo orchioides* (XianMao) 3–5%, *epimedium grandiflorum* (YinYangHuo) 2–5%, *plastrum testudinis* (ShengGuiBan) 4–6%, *Cornus officinalis* (ShanZhuYu) 2–5%, *Psoralea corylifolia* (BuGuZhi) 3–5%, *Leonurus heterophyllus* (YiMuCao) 5–10%.

Alternation #3) The component *Paeonia rubrae* (ChiShao) 5–10% can be added to the formula. It can also be replaced by any of the following, *Paeonia lactiflora* (Bai shao) or *Gelatinum corii* Asini (E Jiao) without changing its weight ratio of weight in the formulation.

Alternation #4) The component *Psoralea corylifolia* (BuGuZhi) 3–5% can be added to the formula. It can also be replaced by any of the following, *Cuscuta chinensis* (TuSiZi), Semen *Astragali Complanati* (ZhongJiLi) or *Eucommia ulmoidis* (DuZhong) without changing its weight ratio of weight in the formulation.

Alternation #5) The component *Astragalus membranaceus* (HuangQi) 7–20% can be added to the formula. It can also be replaced by any of the following, Radix *codonopsis pilosulae* (Dang Shen), Radix Ginseng (Ren Shen).

This invention provides a number of practical examples for this formulation (For the sake of public safety: please note the important warning/disclaimer after the examples)

EXAMPLE 1

Radix *angelica sinensis* (DangGui) 29.3%,
*Ligusticum chuanxiong* (ChuanXiong) 7.3%,
Hirudo (ShuiZhi) 3.7%,
*Astragalus membranaceus* (HuangQi) 11%,
*Paeonia rubrae* (ChiShao) 7.3%,
*Lycium chinense* mill (GouQiZi) 4.4%,
*Polygonatum sibiricum* (HuangJing) 7.3%,
*Curculigo orchioides* (XianMao) 3.3%,
*Epimedium grandiflorum* (YinYangHuo) 3.3%,
*Plastrum testudinis* (ShengGuiBan) 5.5%,
*Cornus officinalis* (ShanZhuYu) 3.7%,
*Psoralea corylifolia* (BuGuZhi) 4.4%,
*Leonurus heterophyllus* (YiMuCao) 7.3%,
*Glycyrrhiza uralensis* (Gancao) 2.2%.

EXAMPLE 2

Radix *angelica sinensis* (DangGui) 28%,
*Ligusticum chuanxiong* (ChuanXiong) 6%,
Hirudo (ShuiZhi) 5%,
*Astragalus membranaceus* (HuangQi) 11%,
*Paeonia rubrae* (ChiShao) 6%,
*Lycium chinense* mill (GouQiZi) 5%,
*Polygonatum sibiricum* (HuangJing) 6%,
*Curculigo orchioides* (XianMao) 5%,
*Epimedium grandiflorum* (YinYangHuo) 5%,
*Plastrum testudinis* (ShengGuiBan) 4%,
*Cornus officinalis* (ShanZhuYu) 5%,
*Psoralea corylifolia* (BuGuZhi) 5%,
*Leonurus heterophyllus* (YiMuCao) 6%,
*Glycyrrhiza uralensis* (Gancao) 3%.

EXAMPLE 3

Radix *angelica sinensis* (DangGui) 21%,
*Carthamus timctorius* (Hong Hua) 10%,
Hirudo (ShuiZhi) 3.3%,
*Astragalus membranaceus* (HuangQi) 14.5%,
*Paeonia lactiflora* (Bai shao) 10%,
*Lycium chinense* mill (GouQiZi) 3.5%,
*Polygonatum sibiricum* (HuangJing) 10%,
*Curculigo orchioides* (XianMao) 3.3%,
*Epimedium grandiflorum* (YinYangHuo) 3%,
*Plastrum testudinis* (ShengGuiBan) 4.4%,
*Cornus officinalis* (ShanZhuYu) 3%,
*Cuscuta chinensis* (TuSiZi) 3.3%,
*Leonurus heterophyllus* (YiMuCao) 8.7%,
*Glycyrrhiza uralensis* (Gancao) 2%

EXAMPLE 4

Radix *angelica sinensis* (DangGui) 38%,
*Prunus persica* (Tao Ren) 5.2%,
Hirudo (ShuiZhi) 4.8%,
*Astragalus membranaceus* (HuangQi) 10%,
*Gelatinum corii* Asini (E Jiao) 5.2%,
*Lycium chinense* mill (GouQiZi) 4.8%,
*Polygonatum sibiricum* (HuangJing) 5.2%,
*Curculigo orchioides* (XianMao) 4.8%,
*Epimedium grandiflorum* (YinYangHuo) 2.2%,
*Plastrum testudinis* (ShengGuiBan) 5%,
*Cornus officinalis* (ShanZhuYu) 2.2%,
Semen *Astragali Complanati* 4.8%,
*Leonurus heterophyllus* (YiMuCao) 5.2%,
*Glycyrrhiza uralensis* (Gancao) 2.6%

EXAMPLE 5

Radix *angelica sinensis* (DangGui) 25%,
*Ligusticum chuanxiong* 8.5%,
Hirudo (ShuiZhi) 4%,

*Astragalus membranaceus* (HuangQi) 9%,
ZiHeChe 9%,
*Lycium chinense* mill (GouQiZi) 4%,
*Polygonatum sibiricum* (HuangJing) 8.5%,
*Curculigo orchioides* (XianMao) 4%,
*Epimedium grandiflorum* (YinYangHuo) 4%,
*Plastrum testudinis* (ShengGuiBan) 6%,
*Cornus officinalis* (ShanZhuYu) 4%,
*Eucommia ulmoidis* (DuZhong) 4%,
*Leonurus heterophyllus* (YiMuCao) 8.5%,
*Glycyrrhiza uralensis* (Gancao) 2.6%.

EXAMPLE 6

Radix *angelica sinensis* (DangGui) 32%,
*Achyrantes bidentata* (Huai Nuxi) 7%,
Hirudo (Shuizhi) 4%,
*Astragalus membranaceus* (HuangQi) 12%,
*Paeonia rubrae* (ChiShao) 7%,
*Lycium chinense* mill (GouQiZi) 3%,
*Polygonatum sibiricum* (HuangJing) 7%,
*Curculigo orchioides* (XianMao) 4%,
*Epimedium grandiflorum* (YinYangHuo) 2.5%,
*Plastrum testudinis* (ShengGuiBan) 4.5%,
*Cornus officinalis* (ShanZhuYu) 2.5%,
*Psoralea corylifolia* (BuGuZhi) 4%,
*Leonurus heterophyllus* (YiMuCao) 6.5%,
*Glycyrrhiza uralensis* (Gancao) 3.5%.

The disclosure of the above practical examples was solely for the purpose of fulfilling the requirements of patent application, and was not intended in any way for the purpose of public use without medical advice, due to the potential risks resulting from the unsupervised combined use of this herbal formulation with other drugs or supplements and many other potential risks involved. Considering the potential public interest in these practical examples, the applicant is obliged to make the following statements: This formulation was designed to be used alone without anticipating further combination with other drugs or supplements without medical supervision. Furthermore, people with certain medical conditions may put themselves at risk by using this product: i.e. (a) people with hypertension with blood pressure above 150/90 mmHg may put themselves at risk by taking this formulation without first lowing their blood pressure to a clinically safe level; (b) people with problems with blood clotting (i.e. bleeding tendency) may put themselves at risk by taking this product due to the anti-coagulating effect of this formulation; (c) Women in pregnancy or lactation should not use this formulation. The only known side-effect of this formulation in people with suitable medical conditions (according to the experience of more than 25 years) has been an increased bowel movement, a problem which will usually resolve by itself within the first one or two weeks' usage. Despite the anti-coagulation effect of the formulation, no bleeding tendency has been reported so far from our long-term experience. As a precaution, if this formulation is to be used in a longer term, a break of at least one-week is needed after every three-month usage to minimize the chance of any potential problem.

For the most commonly used method of preparation: The above formulation can be prepared according to the recommended daily dosage of 270–280 grams for adult. This dosage can be used as a rule for making preparations of larger scales. All raw ingredients should either be in sliced forms, or crushed into smaller pieces to allow thorough extraction of active ingredients from the raw materials through boiling in water. Most raw ingredients are commercially available in a desirable conditions as described above. This formulation has been in the past been prepared as a liquor decoction or a concentrated form (cube or tar form) using the conventional methods. The extraction can be carried out by having the raw materials submerged in water, and boiled for 20 minutes; after removing liquor from the raw material, the raw material should be boiled again in water for another 20 minutes. Liquor from the two boiling (after mixing and filtering through a cloth strainer) can be consumed orally after cooling. If preferred, liquor from the second boiling can be boiled down through evaporation to reduce its liquor volume before being combined with the liquid from the first boiling; To make the formula more easily consumable, the liquor extracted as above can be concentrated to dryness by lyophilization (freeze-drying). Appropriate pharmaceutically acceptable carriers can then be added to yield the cube or tar form, or any other acceptable forms. The route of administration is usually oral (2–3 times/day); however, other routes of administration (e.g. intra-rectally, intraperitoneally, intravenously, intramuscularly, etc.) may also be used if necessary.

This invention is for the treatment of all types of neuronal injuries and neurodegenerative diseases in a subject by administrating to the subject an effective amount of the above pharmaceutical compositions. Clinical data accumulated over the last 25–30 years have demonstrated the effectiveness of this formulation in treating children feeble-mindedness (or mental retardation), cerebral palsies, paralysis caused by head trauma or toxic chemicals as well as infectious agents, motor neuron disease, senile dementia, or post-encephalitis dementia, cerebral atrophy, oliverpontocerebellar atrophy, ataxia, etc. Owing to the clinical effectiveness of this formulation so far in neuronal injuries of almost all causes, and many anecdotal cases, this formulation will also have a beneficial effect on those neurodegenerative diseases so far not been tested in well controlled clinical trials. These diseases include but not limited to, Alzheimer's disease, Parkinson's disease, Huntington's disease, AIDS dementia and many other type of neurodegenerative diseases.

The daily dosage (270–300 g raw materials) of this formulation may be contained in the 2 cubes (two tars):

For Adults:

With a body weight of 50–60 Kg, 2 cube/day orally will be the recommended dosage. For adults with higher body weight or in more severe conditions, 3 cubes/day can be used. Since its proven safety in the toxicity test, it is anticipated that the daily dosage can be increased even further. However, it is not recommended to go beyond this 3-cubes/day dosage without appropriate medical monitoring to avoid unnecessary and unpredictable side effects.

For Children: the recommended daily dosage

<3 years: 0.5–1 cube/day (¼–½ of the average adult dosage)

3–6 years: 1 cube/day (½ of the average adult dosage)

>6 years: 1–2 cubes/day (½ of or equal to the average adult dosage).

For non-human subjects: the human dosage serves as a guide. The effective dosage may vary in each individual subject and disease.

This invention is further used for treating or alleviating inflammation or allergic reaction in a subject by administrating to the subject an effective amount of the above pharmaceutical compositions. The above dosage can be used as a guide for this formulation. The effective dosage varies depending on each situation.

This invention is further used for treating or alleviating delayed-type hypersensitivity (DTH) in a subject by administrating to the subject an effective amount of the above pharmaceutical compositions. The above dosage can be used as a guide for this formulation. The effective dosage can vary depending on each situation.

This invention is further used for its potent immunoregulatory effect in a subject by administrating to the subject an effective amount of the above pharmaceutical compositions. The above dosage can be used as a guide for this formulation. The effective dosage can vary depending on each situation.

This invention further increases the post-immunization antibody production in a subject by administrating to the subject an effective amount of the above pharmaceutical compositions. The above dosage can be used as a guide for this formulation. The effective dosage can vary depending on each situation.

This invention further reduces the viscosity of blood and plasma in a subject by administrating to the subject an effective amount of the above pharmaceutical compositions. The above dosage can be used as a guide for this formulation. The effective dosage can vary depending on each situation.

This invention further inhibits platelet aggregation and has a de-aggregating effect on the already formed platelet aggregates in a subject by administrating to the subject an effective amount of the above pharmaceutical compositions. The above dosage can be used as a guide for this formulation. The effective dosage can vary depending on each situation.

This invention further improves blood circulation, microcirculation of the whole body in a subject by administrating to the subject an effective amount of the above pharmaceutical compositions. The above dosage can be used as a guide for this formulation. The effective dosage varies in each situation.

This invention further improves brain blood flow in a subject by administrating to the subject an effective amount of the above pharmaceutical compositions. The above dosage can be used as a guide for this formulation. The effective dosage varies in each situation.

This invention provides a theory of Chinese Medicine based on which this formulation was designed for the treatment of above diseases and conditions. Radix *Angelica Sinensis* (DangGui) was used as the major component (the king component) for blood nourishment and mobilization; *Ligusticum chuanxiong* (ChuanXiong), *Astragalus membranaceus* (HuangQi) and *Paeonia rubrae* (ChiShao) for Qi nourishment and blood mobilization; *Lycium chinense* mill (GouQiZi), *Polygonatum sibiricum* (HuangJing), *Curculigo orchioides* (XianMao), *Epimedium grandiflorum* (YinYangHuo), *Plastrum testudinis* (GuiBan), *Cornus officinalis* (ShanZhuYu), *Psoralea corylifolia* (BuGuZhi) and *Leonurus heterophyllus* (YiMuCao) for the nourishment of liver and kidney; Hirudo (ShuiZhi) to strengthen the effect of blood mobilization; *Glycyrrhiza uralensis* to modulate the effect of all the components. This combination in synergy has the effects for Qi nourishment, blood mobilization, and the nourishment of liver and kidney.

This invention provides a method of preparation for this formulation.

This invention provides a formulation prepared according to the above method, which comprises an effective amount of the above compositions and a pharmaceutical acceptable carrier.

This invention provides that this formulation includes but is not limited to the form of pill, capsule, granule, tablet, suspension, injection, syrup, tincture, and adhesive plaster.

For the purposes of this invention, "pharmaceutically acceptable carriers" means any of the standard pharmaceutical carriers. Examples of suitable carriers are well known in the art and may include, but not be limited to, any of the standard pharmaceutical carriers such as a phosphate buffered saline solution and various wetting agents. Other carriers may include additives used in tablets, granules and capsules, etc. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well known conventional methods.

This invention provides a method for treating neuronal injuries of all causes in a subject by administrating to the subject an effective amount of the above pharmaceutical compositions.

This invention provides a method for treating paralysis caused by all causes (i.e. head trauma) in a subject by administrating to the subject an effective amount of the above pharmaceutical compositions.

This invention provides a method for treating feeblemindedness (or mental retardation) in a subject by administrating to the subject an effective amount of the above pharmaceutical compositions.

This invention provides a method for treating cerebral palsies in a subject by administrating to the subject an effective amount of the above pharmaceutical compositions.

This invention provides a method for treating all types of neurodegenerative diseases as well as neurodegenerative conditions in a subject by administrating to the subject an effective amount of the above pharmaceutical compositions.

This invention provides a method for treating Motor Neuron disease in a subject by administrating to the subject an effective amount of the above pharmaceutical compositions.

This invention provides a method for treating dementia of all causes (e.g. vascular dementia, Alzheimer disease, post-encephalitis dementia, etc.) in a subject by administrating to the subject an effective amount of the above pharmaceutical compositions.

This invention provides a method for treating cerebral atrophy in a subject by administrating to the subject an effective amount of the above pharmaceutical compositions.

This invention provides a method for treating ataxia of all causes in a subject by administrating to the subject an effective amount of the above pharmaceutical compositions.

This invention provides a method for treating vegetative state in a subject by administrating to the subject an effective amount of the above pharmaceutical compositions.

This invention provides a method for treating or alleviating inflammation or allergic reaction in a subject by administrating to the subject an effective amount of the above pharmaceutical compositions.

This invention provides a method for treating or alleviating all autoimmune diseases as well as autoimmune conditions in a subject by administrating to the subject an effective amount of the above pharmaceutical compositions.

This invention provides a method for treating or alleviating multiple sclerosis in a subject by administrating to the subject an effective amount of the above pharmaceutical compositions.

This invention provides a method for sequel of apoplexy in a subject by administrating to the subject an effective amount of the above pharmaceutical compositions.

This invention provides a method for treating myelitis in a subject by administrating to the subject an effective amount of the above pharmaceutical compositions.

This invention provides a method for polyneuritis in a subject by administrating to the subject an effective amount of the above pharmaceutical compositions.

This invention provides a method for muscle-stiffness in a subject by administrating to the subject an effective amount of the above pharmaceutical compositions.

This invention provides a method for muscle spasm in a subject by administrating to the subject an effective amount of the above pharmaceutical compositions.

This invention provides a method for arthritis in a subject by administrating to the subject an effective amount of the above pharmaceutical compositions.

This invention provides a method for reducing the viscosity of blood and plasma in a subject by administrating to the subject an effective amount of the above pharmaceutical compositions.

This invention provides a method for inhibiting platelet aggregation induced in a subject by administrating to the subject an effective amount of the above pharmaceutical compositions.

This invention provides a method for de-aggregating the already formed platelet aggregates in a subject by administrating to the subject an effective amount of the above pharmaceutical compositions.

This invention provides a method for increasing the diameter of the collective capillary and count of the microvessel opening in a subject by administrating to the subject an effective amount of the above pharmaceutical compositions.

This invention provides a method for prolonging the latent period for adrenaline-induced blood vessel constriction, and countering the microvessel closure induced by adrenaline in a subject by administrating to the subject an effective amount of the above pharmaceutical compositions.

This invention provides a method for significantly increasing the blood flow in brain in a subject by administrating to the subject an effective amount of the above pharmaceutical compositions.

This invention provides a method for significantly increasing the microcirculation in the brain in a subject by administrating to the subject an effective amount of the above pharmaceutical compositions.

This invention provides a method for inhibiting delayed-type hypersensitivity (DTH) response in a subject by administrating to the subject an effective amount of the above pharmaceutical compositions.

This invention provides a method for increasing the post-immunization antibody production in a subject by administrating to the subject an effective amount of the above pharmaceutical compositions.

This invention provides a method for immunoregulation in a subject by administrating to the subject an effective amount of the above pharmaceutical compositions.

EXPERIMENTAL DETAILS

Preparation of this Formulation

1. Preparation of the Raw Materials

All raw material should be either in sliced form, or crushed into smaller pieces for allowing the thorough extraction of ingredients from the raw materials by boiling. Each day's dosage is generally 270–300 g of raw materials.

2. Extraction

This formulation can be prepared as the liquor decoction or the concentrated form (the cube or tar form) using the conventional methods. The extraction was carried out by boiling the combination in water twice, 20 minutes each time; the liquor from the two boiling can be directly used (the liquor decoction)

3. Evaporation or Lyophilization

The combined liquor from the two boiling can then be filtered using a cloth strainer, and then be concentrated to dryness by lyophilization (freeze-drying). Appropriate pharmaceutically acceptable carriers can then be added to yield the cube or tar form, or any other acceptable forms.

Pharmacological Effects of this Formulation (30)

Animals Used:

KunMing mice, body weight 20+/−2 g;

Wistar rat, body weight 180+/−20 g;

Wild type dog 8.0+/−1 Kg.

All animals include both male and females.

Bu-Nao-Gao was dissolved in distilled water to make a 40% solution. The exact formulation of Bu-Nao-Gao used in all the pharmacological studies is illustrated in Example 1 (extract from 273 g raw materials was contained in the two cubes).

1. Effects on Blood Viscosity 40 rats were randomly distributed into 4 groups, orally given Bu-Nao-Gao 4.8 g/kg or equal volume of saline for 6 days. On day 7, 5 ml of blood was taken from the common carotid artery.

TABLE 1

Effects of Bu-Nao-Gao on blood viscosity

| Groups | Control | Bu-Nao-Gao | Bu-Nao-Gao |
|---|---|---|---|
| Dosage (g/kg) | | 4 | 8 |
| Whole blood viscosity (x +/− SD) | | | |
| Low cut (200S-1) | 7.97 +/− 0.38 | 5.35 +/− 0.42 | 5.90 +/− 0.58 |
| High cut (2000S-1) | 4.78 +/− 0.51 | 3.37 +/− 0.37 | 3.39 +/− 0.28 |
| Plasma viscosity (x +/− SD) | 1.93 +/− 0.14 | 1.42 +/− 0.13 | 1.44 +/− 0.15 |
| Electrophoresis of erythrocytes (x +/− SD) | 19.18 +/− 0.13 | 18.23 +/− 0.38 | 16.8 +/− 0.45 |

2. Effects on Platelet Aggregation Induced by ADP

Method: Modified according to Born's method (31)

Results: see Table 2.

3. Effects on Platelet De-Aggregation

Method: Modified according to the method by Parise et al. (31).

Results: see Table 2.

TABLE 2

Effects of Bu-Nao-Gao on platelet aggregation induced by ADP and on platelet de-aggregation in rats (n = 5)

| Groups | Dosage (g/dl) | Aggregation | | De-aggregation | |
|---|---|---|---|---|---|
| | | curve decline (x +/− SD mm) | rate of inhibition (%) | elevation curve (x +/− SD mm) | rate of deaggregation (%) |
| Saline | | 78.2 +/− 3.4 | 0 | 0 | 0 |
| Bu-Nao-Gao | 2.5 | 63.7 +/− 2.8* | 18.5 | 35.3 +/− 3.2** | 54.4 |
| | 5.0 | 51.5 +/− 7.1** | 34.1 | 38.7 +/− 4.6** | 66.2 |
| | 10.0 | 25.8 +/− 4.4** | 67.0 | 41.6 +/− 5.1** | 72.3 |
| | 20.0 | 9.2 +/− 5.2** | 88.2 | 48.2 +/− 4.2** | 73.9 |

*P < 0.05
**P < 0.001

4. Effects on Microcirculation in Mice 50 mice were randomly distributed into 5 groups (n=10). After Wu-La-tan (1 g/Kg) injection peritoneally, mice were anesthetized and their ears were examined under microscope (50×) for the collective capillaries. Crossing points between capillaries and transitional blood vessels were counted as the number of blood vessel opening. Bu-Nao-Gao was given intraperitoneally at 4 g/kg, counts of blood vessel opening were calculated before and 10 minutes after the injection. Intraperitoneal injection of saline was used as the control.

4.1. Effects on the Capillary Diameter

After 10 minutes of given Bu-Nao-Gao, the capillary diameter increased 11.7+/−8.4 (%), the change in the control group was −1.4%+/−3.3. Therefore Bu-Nao-Gao was demonstrated to be able to significantly increase the capillary diameter (P<0.001).

4.2. Effects on Blood Vessel Constriction Induced by Adrenaline

After 10 minutes of given Bu-Nao-Gao, adrenaline was injected intraperitoneally at 10 μg/kg. The latent period of capillary constriction was 124+/−7.6 seconds in Bu-Nao-Gao group, and 102+/−46 seconds in control group. This demonstrated that Bu-Nao-Gao can significantly prolong the latent period of capillary constriction induced by adrenaline (P<0.01).

4.3. Effects on Microvessel Opening

After 10 minutes of given Bu-Nao-Gao, the change for microvessel opening was 12.8%+/−7.6. The change for the control group was −2.1%+/−4.3. This demonstrated that Bu-Nao-Gao can significantly increase the number of microvessel opening (P<0.001).

4.4. Effects on the Microvessel Closure Induced by Adrenaline

After given adrenaline, the change for microvessel opening in Bu-Nao-Gao group was −3.3%+/−10.2, and in control group was −32.6+/−11.0. This demonstrated that Bu-Nao-Gao can significantly hinder microvessel closure induced by adrenaline (P<0.01).

5. Effects on Blood Supply to Brain in Dogs

This effect was evaluated in 15 anesthetized healthy dogs (in a lying on back position). Left common carotid artery was exposed for 3 cm, after closing the left external carotid artery and vertebrate artery, average blood flow (ml/min) in the internal carotid artery was measured. Bu-Nao-Gao was given intravenously through the right jugular vein. The whole brain was later removed above the level of medullar, and measured for its total weight.

$$\text{Brain blood flow}(ml/100\ g.\ min) = \frac{\text{average blood flow}}{\text{half brain weight}} \times 100$$

TABLE 3

Effects of Bu-Nao-Gao on brain blood flow in dog (n = 5)

| Groups | Saline | Bu-Nao-Gao |
|---|---|---|
| dosage (g/dl) | | 4.0 |
| Before ml/100 g. | 352 +/− 40 | 360 +/− 24 |
| After | | |
| 3 min | 352 +/− 40 | 428 +/− 61* |
| 5 min | 350 +/− 76 | 427 +/− 45* |
| 10 min | 352 +/− 63 | 487 +/− 49** |
| 15 min | 351 +/− 77 | 424 +/− 67* |
| 20 min | 352 +/− 45 | 424 +/− 91* |
| 30 min | 351 +/− 66 | 412 +/− 77 |
| 60 min | 352 +/− 48 | 408 +/− 63 |

*P < 0.01
**P < 0.001

6. Effects on the Weight of Immune Organs

Mice were randomly distributed, and were given Bu-Nao-Gao (4 g/Kg) orally, or hydrocortison (50 mg/Kg) or saline intramuscularly, for seven days. 24 hours after the last administration, mice were sacrificed. The weight of each organ/total body weight was demonstrated as index of each organ.

TABLE 4

Effects of Bu-Nao-Gao on the weight of immune organs (n = 15)

| Groups | Dosage (g/kgxd) | Index of immune organ (mg/g X +/− SD) | |
|---|---|---|---|
| | | Spleen | thymus |
| Saline | equal vol. | 3.74 +/− 0.71 | 2.76 +/− 0.60 |
| Bu-Nao-Gao | 4.0 | 4.28 +/− 1.10 | 1.41 +/− 0.72 |
| Hydrocortisone | 0.05 | 2.66 +/− 0.40 | 1.37 +/− 0.26 |

7. Effects on Antibody Production in Mice

Mice were randomly distributed, and were given Bu-Nao-Gao (4 g/Kg) orally, or hydrocortison (50 mg/Kg) or saline intramuscularly, for seven days. On day 2, they were immunized with 10% sheep erythrocytes intra-peritoneally. On day 8, erythrocyte agglutination as well as cell lysis were measured respectively.

TABLE 5

Effects of Bu-Nao-Gao on antibody production (n = 15)

| Groups | Dosage (g/kgxd) | Agglutinin (33) (HC$_{50}$) | Erythorcytolysin (32) |
|---|---|---|---|
| Saline | equal vol. | 167.5 +/− 18.9 | 43.6 +/− 2.5 |
| Bu-Nao-Gao | 4.0 | 194.0 +/− 16.4 | 52.9 +/− 2.5 |
| Hydrocortisone | 0.05 | 126.7 +/− 19.3 | 37.5 +/− 4.2 |

8. Effects on Delayed-Type Hypersensitivity (DTH)

Mice were given Bu-Nao-Gao (oral at 4 g/Kg daily), or cyclophosphomide (0.03 g/kg, intramuscularly every other day) or saline (oral, daily). On day 3, mice were given 0.02 ml of 7% DNCB subcutaneously on the back, and were boosted three days later in the same way. 9 days later, 0.02 ml of 1% DNCB was applied to the left ear. This area was removed by a ear puncher of 9 mm diameter and the extent of ear swelling represents the extent of delayed-type hypersensitivity (for results, see Table 6).

The extent of swolleness (%) =

$$\frac{\text{weight of the left ear piece} - \text{weight of right ear piece}}{\text{weight of right ear piece}}$$

TABLE 6

Effects of Bu-Nao-Gao on cellular immunity (n = 15)

| Groups | Dosage (g/kg) | NBT (%) | ANAE (%) | DNCB (extent of swolleness) |
|---|---|---|---|---|
| Saline | equal vol. | 6.0 +/− 1.9 | 50.1 +/− 9.4 | 20.94 +/− 8.41 |
| Bu-Nao-Gao | 4.0 | 13.4 +/− 4.0 | 42.3 +/− 11.5 | 12.47 +/− 8.24 |
| cyclo-phosphamidum | 0.03 | ND | ND | 12.26 +/− 8.8 |

9. Effects on NBT Reductive Response of Neutrophils

By using the same strategy of drug delivery as above, blood was collected from postocular vein for the NBT reductive response of neutrophils (34) (Table 6).

10. Effects on ANAE Staining of Peripheral Blood Lymphocytes

By using the same strategy of drug delivery as above, blood was collected from mouse tails for ANAE staining of periphery blood lymphocytes (Table 6).

11. Toxicity Tests 11.1. Acute Toxicity 30 mice fed by Bu-Nao-Gao at maximum concentration and maximum volume (100%, 50 mg/kg) through feeding tube into the stomach, twice daily for 7 days. No death occurred. This is a dosage 310 time the dosage used in human adult (50 kg). Therefore this experiment provided a strong support for Bu-Nao-Gao's safe use in human.

11.2. Chronic Toxicity 20 rats, randomly distributed into two groups (half male, half female), were fed by Bu-Nao-Gao at 4 g/kg or equal volume of saline twice daily, for three months. Mice were monitored for survival, food intake, movement, and body weight. Three months later, blood routine and SGPT were tested, heart, liver, spleen, lung, kidney, adrenal gland and brain were fixed by methanol for histology. All mice survived, there was no negative effect on their food intake, movement and growth. Results of routine blood test and SGPT were all within normal ranges. Histological examinations of all above organs revealed no abnormality.

12. Summary and Discussion

Here Bu-Nao-Gao is shown to significantly reduce the viscosity of whole blood and plasma; to shorten the electrophoresis time of erythrocytes; to significantly inhibit the platelet aggregation induced by ADP; to have a very clear de-aggregating effect on platelet aggregates induced by ADP; to significantly increase the diameter of the collective capillary and increase the count of microvessel opening; to significantly prolong the latent period of adrenaline-induced blood vessel constriction, to counter the adrenaline-induced microvessel closure; to significantly increase brain blood flow of anesthetized dogs; to increase the post-immunization antibody production in mice; to significantly inhibit the DNCB-induced delayed-type hypersensitivity; to increase the ratio of NBT-positive eosinophils in peripheral blood; to have no obvious effect on ANAE staining of lymphocytes.

The above data suggests that the beneficial effects of Bu-Nao-Gao on neuronal injuries resulting from many causes was probably due to its effects on improving blood circulation, on increasing the exchange between blood and extracellular space of cells, therefore allowed sufficient blood supply to the brain, or the region of injuries. Bu-Nao-Gao also has a potent immune regulatory effects: on the one hand, it can increase the post-immunization antibody production, enhance the activity of phagocytes (beneficial for the localization and absorption of inflammation); on the other hand, it can inhibit delayed-type hypersensitivity, and have anti-inflammatory and anti-allergic effects. Its potent regulatory effect helps to keep the body's defense mechanisms in a balanced state. This potent immune regulatory role may also be an important mechanism behind its efficacy in so many diseases or pathological conditions. In addition, Bu-Nao-Gao is very likely to have a potent effect on promoting neuronal regeneration as well as regeneration of other damaged cells. However, limited by our experimental capacity, no experimental evidence is so far available to prove this assumption.

Bu-Nao-Gao showed no toxicity after the short-term use of large dose in mouse (one week, 310 time the adult human dosage), and long-term use (normal adult human dosage for three months in rats). No toxic effect has ever been reported in inventor's more than 25 years of clinical experience.

Experimental Studies on the Large-Dosage Single Usage of Radix *angelica sinensis* (35)

Ingredient: Angelica sinensis prepared as liquor decoction.

Patients: Total 218 patients tested: female 87, male 131; age in range 18 to 80 years of age; 56 patients took Radix *angelica sinensis* 30–59 g/day for one month; 162 patients took Radix *angelica sinensis* 60–90 g/day for one month.

No side effect was observed both clinically and by various tests on blood, liver, heart, kidney functions Acute toxicity test (in mice): Large dosage of Radix *angelica sinensis* was given orally to 20 KuenMing mice for 7 days. The largest tolerable dosage given to mice (400 g raw ingredient/Kg) was equivalent to 166 times of the adult human dosage. No death occurred at this dosage. LD50 could not be found by the use of this single ingredient.

Chronic toxicity test (in rat): at the daily dosage of 15 g (raw material)/kg and 40 g (raw material)/kg for 60 days. No abnormality was observed in any of the following parameters such as body weight, behavior, routine blood test (heart, liver, kidney functions), histology, etc.

Clinical Studies

Unless otherwise indicated, the exact formulation of Bu-Nao-Gao used in most of the clinical studies is illustrated in Example 1 (extract from 273 g raw materials was contained in the two cubes/tar) of the example section.

| Catergories of clinical studies | |
|---|---|
| Study #1. | Treatment of children with feeblemindedness (133 cases) |
| Study #2. | Treatment of children with cerebral palsy (102 cases) |
| Study #3. | Treatment of paralysis resulting from head trauma (66 cases) |
| Study #4. | Treatment of 23 patients of motor neuron disease |
| Study #5. | Treatment of three patients in vegetative state |
| Study #6. | Treatment of Oliverpontocerebellar atrophy (Dejerine-Thomas type, 3 cases) |
| Study #7. | Treatment of hereditary cerebellar ataxia (3 cases) |
| Study #8. | Treatment of dementia |
| Study #9. | Treatment of sequel of apoplexy |
| Study #10. | Treatment of apoplexy combined with pseudo-bulbar palsy |
| Study #11. | Treatment of encephalopathy |
| Study #12. | Treatment of multiple sclerosis (MS) |
| Study #13. | Treatment of myelitis |
| Study #14. | Treatment of polyneuritis |
| Study #15. | Treatment of muscle-stiffness. |
| Study #16. | Treatment of muscle spasm |
| Study #17. | Treatment of giant cell arteritis |

Clinical Study #1: Bu-Nao-Gao in the Treatment of Children with Feeblemindedness (a Trial of 133 Cases)(36)

1.1 General Information

This clinical trial was carried out between January 1989 and December 1992 at the provincial hospital of Chinese Medicine, Lanzhou, GanSu province, P. R. China. The details are listed in Table 7.

TABLE 7

Treatment of children with feeblemindedness with Bu-Nao-Gao

| | Bu-Nao-Gao group | Control group |
|---|---|---|
| Total cases | 75 | 58 |
| Male | 45 | 29 |
| Female | 30 | 29 |
| Range in Age | 4 months to 14 years (5.8 years in average) | 1 year to 14 years (5.9 years in average) |
| Age distribution: | | |
| 0–3 years | 28 | 13 |
| 4–6.5 years | 17 | 20 |
| 6.5 years and above | 30 | 25 |
| IQ (DQ for age <3 years) | | |
| Marginal (IQ 70–79) | 6 | 5 |
| Mild (IQ 55–69) | 18 | 8 |
| Moderate (IQ 40–54) | 16 | 11 |
| Severe (IQ 25–39) | 20 | 9 |
| Most severe (IQ <24) | 15 | 25 |
| Brain CT scan | 26 tested | Not tested |
| Cortical atrophy: | 12 | |
| localized region of reduced densities | 5 | |
| localized region of high density | 1 | |
| Cerebellum atrophy | 1 | |
| Arachinoidal cyst | 2 | |
| Normal | 4 | |

TABLE 7-continued

Treatment of children with feeblemindedness with Bu-Nao-Gao

| | Bu-Nao-Gao group | Control group |
|---|---|---|
| Electroencephalography (EEG) | 16 tested | Not tested |
| Mildly abnormal | 3 | |
| Moderately abnormal | 7 | |
| Highly abnormal | 6 | |
| Complications and concomitant diseases | | |
| Cerebral palsies | 69 | 24 |
| Major epilepsy | 17 | |
| Minor epilepsy | 2 | 1 |
| Myoclonic epilepsy | 6 | 2 |
| spontaneous movement | 6 | |
| Congenital heart disease | 1 | 1 |
| Congenital lip cleft | | 4 |
| Etiology | | not available |
| Premature birth | 15 | (because all cases |
| Hypoxia during delivery | 23 | were from the city's |
| Cesarean section | 3 | orphanage hospital) |
| Sequel of nuclear Jaundice | 3 | |
| Maternal history of severe infection | 3 | |
| Sign of embryonic abortion | 1 | |
| Unknown | 27 | |

1.2 Treatment Strategy (Table 8).

TABLE 8

Treatment Strategy of Bu-Nao-Gao vs. control groups for feeblemindedness

| | Bu-Nao-Gao group Oral intake of Bu-Nao-Gao alone No additional training or other medications | Control Oral intake of An-Fu-Kang* some also combined with acupuncture, massage or planned exercises |
|---|---|---|
| Hospitalized | 23 cases | 58 cases (in the orphanage hospital) |
| Out-patients | 52 cases | |
| Dosage | <3 yr.: 0.5–1 cube/day | <5 yrs: 0.8–1.2 g/day |
| | 3–6 yrs: 1 cube/day | 5–10 yrs: 1.8 g/day |
| | >6 yrs: 1–2 cubes/day | >10 yrs: 2.4 g/day |
| Duration of treatment | | |
| 1 month | 24 cases | |
| 2 months | 25 cases | |
| 3 months | 14 cases | 58 cases |
| 4 months | 9 cases | |
| 6 months | 3 cases | |

*Nao-Fu-Kong is a commercially available herbal decoction commonly used for brain dysfunctions.

1.3 Criteria for Clinical Evaluation Diagnostic Criteria for Feeblemindedness
(1) Intelligence obviously below average: IQ lower than average minus 2 SD (IQ<70, SD=15).
(2) Deficits in age-appropriate behaviors.
(3) At developmental stage (less than 18 years of age)

All children who entered the study satisfied the above three criteria.

Measurement of Intelligence
(1) Gesell criteria: children of 4 weeks-3 years of age were evaluated with this criteria (2) WPPSI criteria: 4–6.5 years of age
(3) WISC-R criteria: 6.5–16 years of age.

Criteria for Evaluating Therapeutic Effects
 (IQ was determined according to international standards)
Notable effect: increase of IQ>15 (including 15)
Improvement: increase of IQ 10–14 (including 10)
Effective: increase of IQ 5–9 (including 5)
No effect: increase of IQ<5

1.4 Results (Table 9–12)

TABLE 9

Therapeutic efficacy of Bu-Nao-Gao for children with feeblemindedness

| Effect | Bu-Nao-Gao (%) | Control (%) |
|---|---|---|
| Total cases | 75 | 58 |
| Notable effect | 27 (36%) | 6 (10%) |
| Improvement | 17 (23%) | 7 (12%) |
| Effective | 22 (29%) | 4 (7%) |
| No effect | 9 (12%) | 41 (71%) |
| Total effective | 66 (88%) | 17 (29%) |

TABLE 10

Total effective rate of Bu-Nao-Gao and control groups for feeblemindedness of different severities

| | Total effective rate | |
|---|---|---|
| Severity | Bu-Nao-Gao | Control |
| total cases | 75 | 58 |
| Marginal | 5/6 (83%) | 4/5 (80%) |
| mild | 18/18 (100%) | 2/8 (25%) |
| moderate | 16/16 (100%) | 5/11 (45%) |
| severe | 16/20 (80%) | 5/9 (55%) |
| most severe | 11/15 (73%) | 1/25 (4%) |
| total | 66/75 (88%) | 17/58 (29.3%) |

Total effective rate includes the rates of notable effect, improvement and effective

TABLE 11

Analysis of Bu-Nao-Gao for feeblemindedness of different severities (75 cases)

| | notable effective | improvement | effective | no effect | total effective |
|---|---|---|---|---|---|
| mild (IQ 55–69) | 6 | 7 | 5 | | 18/18 (100%) |
| moderate (IQ 40–54) | 7 | 3 | 6 | | 16/16 (100%) |
| severe (IQ 25–39) | 6 | 4 | 6 | 4 | 16/20 (80%) |
| most severe (IQ <24) | 5 | 2 | 4 | 4 | 11/15 (73%) |
| marginal (IQ 70–79) | 3 | 1 | 1 | 1 | 5/6 (83%) |
| % of total | 27 (36%) | 17 (22.7%) | 229 (29.3%) | 66 (12%) | (88%) |

TABLE 12

Analysis of Nao-Fu-Kang (control group) for feeblemindedness of different severity (58 cases)

| | notable effective | improvement | no effective | total effect | effective |
|---|---|---|---|---|---|
| mild (IQ 55–69) | 2 | | | 6 | 2/8 (25%) |
| moderate (IQ 40–54) | 2 | 2 | 1 | 6 | 5/11 (45%) |
| severe (IQ 25–39) | 1 | 3 | 1 | 4 | 5/9 (55%) |
| most severe (IQ <24) | | | 1 | 24 | 1/25 (4%) |
| marginal (IQ 70–79) | 1 | 2 | 1 | 1 | 4/5 (80%) |
| % of Total | 6 (10.3%) | 17 (12.1%) | 4 (7%) | 41 (70.7%) | 17 (29.3%) |

1.5 Clinical Follow-Up 50 out of 75 cases in the Bu-Nao-Gao group were followed up for a period of 3 months to 4 years, the intelligence of all patients were found in stable conditions or had continued improvement. No single case of deterioration was reported during this period.

1.6 Conclusion and Remarks

For the treatment of children feeblemindedness using Bu-Nao-Gao: The rate for notable effective is significantly higher in Bu-Nao-Gao group (36%) than that of the control group (10%). P<0.001.

The total effective rate of the Bu-Nao-Gao group (88%) is significantly higher than that of the control group (29%). P<0.001.

For mild type, the total effective rate of the Bu-Nao-Gao group (100%) is significantly higher than that of the control group (25%). P<0.001.

For moderate type, the total effective rate of the Bu-Nao-Gao group (100%) is significantly higher than that of the control group (45%). P<0.01.

For severe and most severe types, the total effective rate of the Bu-Nao-Gao group (77.1%) is significantly higher than that of the control group (18%). P<0.01.

Therefore Bu-Nao-Gao is found to have significant therapeutic effect on children feeblemindedness.

Clinical Study #2. Bu-Nao-Gao in the Treatment of Children with Cerebral Palsy (a Trial of 102 Cases)(37)

2.1 General Information

This clinical trial was carried out between January 1989 and December 1992 by the provincial hospital of Chinese Medicine, Lanzhou, GanSu province. The details are listed in Table 13.

TABLE 13

Bu-Nao-Gao and control groups for children with cerebral palsy

| | Bu-Nao-Gao group | Control group |
|---|---|---|
| No. of Cases | 78 | 24 |
| Male | 47 | 14 |
| Female | 31 | 10 |
| Range in Age | 4 months to 13 years (5.9 years in average) | 1 year to 9.5 years (4.1 years in average) |
| Age distribution: | | |
| 0–3 years | 34 | 7 |
| 4–6.5 years | 21 | 11 |
| 6.5 years and above | 23 | 6 |
| Severity by muscle strength | | |
| Mild (III$^+$–V) | 9 (11.5%) | 11 (45.8%) |
| Moderate (II$^+$–III) | 42 (53.8%) | 10 (41.7%) |
| Severe (I$^+$–II) | 24 (30.8%) | 3 (12.5%) |
| Most severe (0–I) | 3 (3.85%) | 0 |
| Type of cerebral palsies | | |
| Spastic type | 59 | 11 |
| Athetosis | 1 | 1 |
| Rigidity | 1 | 1 |
| Ataxic type | 10 | |
| Tremor | 2 | |
| dystonic type | 5 | 11 |
| Severity of paralysis | | |
| Quadriplegia | 64 | 17 |
| Paraplegia | 3 | 3 |
| Hemiplegia | 8 | 3 |
| Monoplegia | 1 | 1 |
| Brain CT scan | 29 tested | not tested |
| Cortical atrophy: | 12 | |
| localized region of reduced densities | 9 | |
| localized region of high density | 1 | |
| Cerebellum atrophy | 1 | |
| Arachinoidal cyst | 2 | |
| Normal | 3 | |

TABLE 13-continued

Bu-Nao-Gao and control groups for children with cerebral palsy

| | Bu-Nao-Gao group | Control group |
|---|---|---|
| Electroencephalography (EEG) | 21 tested | not tested |
| Slightly abnormal | 4 | |
| Moderately abnormal | 11 | |
| Highly abnormal | 6 | |
| Complications & concomitant diseases | | |
| Cerebral feeblemindedness | 68 | 24 |
| Major epilepsies | 20 | |
| pyknolepsy | 2 | 1 |
| Myoclonic epilepsy | 4 | |
| Spontaneous movement | 3 | |
| Congenital heart disease | 1 | 1 |
| Etiology | | not available* (because all cases were from the city's orphanage hospital) |
| Premature birth | 12 | |
| Hypoxia during delivery | 23 | |
| Cesarean section | 3 | |
| Sequel of nuclear jaundice | 3 | |
| Maternal history of severe infections | 5 | |
| Unknown | 30 | |

2.2. Treatment Strategy (Table 14)

TABLE 14

Treatment Strategy for Bu-Nao-Gao vs. control groups for cerebral palsy

| | Bu-Nao-Gao group Oral intake of Bu-Nao-Gao alone No additional training or other medications | Control Oral intake of Nao-Fu-Kang* some also combined with planned exercise, acupuncture, massage |
|---|---|---|
| Total Cases | 78 | 24 |
| Hospitalized | 23 | 24 (in the Orphanage hospital) |
| Out-patients | 55 | |
| Dosage | <3 yrs, 0.5–1 cube/day 3–6 yrs: 1 cube/day >6 yrs: 1–2 cubes/day | <5 yrs, 0.8–1.2 g/day 5–10 yrs: 1.8 g/day >10 yrs: 2.4 g/day |
| Duration of treatment | | |
| 1 month | 24 | |
| 2 months | 32 | |
| 3 months | 20 | 24 |
| 4 months | 2 | |

*Nao-Fu-Kong is a commercially available herbal decoction commonly used for brain dysfunction 2.3 Criteria for Clinical Evaluation (the Internationally Used Six Grade Criteria)

Cured: movement become normal, muscle strength reach grade V

Notable effect: movement function significantly improved, muscle strength improved over 2 grade.

Effective: movement function improved, muscle strength improved over 1 grade.

No effect: no improvement of movement function, muscle strength improved less than 1 grade.

2.4. Results (Tables 15–18)

TABLE 15

Therapeutic efficacy of Bu-Nao-Gao for children with cerebral palsy

| Effect | Bu-Nao-Gao (%) | Control (%) |
| --- | --- | --- |
| total Case | 78 | 24 |
| Cured | 7 (9%) | 0 |
| Notable effect | 21 (26.9%) | 1 (4.2%) |
| Effective | 46 (59%) | 4 (16.7%) |
| No effect | 4 (5.1%) | 19 (79.2%) |
| Total effective | 74 (98.9%) | 5 (20.8%) |

TABLE 16

Total effective rate of Bu-Nao-Gao and control for cerebral palsy of different severities

| Severity | Total effective rate Bu-Nao-Gao | Total effective rate Control |
| --- | --- | --- |
| total cases | 78 | 24 |
| mild | 8/9 (88.9%) | 4/11 (36.4%) |
| moderate | 39/42 (92.9%) | 1/10 (10%) |
| severe | 24/24 (100%) | 0/3 (0) |
| most severe | 3/3 (100%) | 0 (0) |
| total | 74/78 (94.9%) | 5/24 (20.8%) |

Total effective rate includes the rate of cured, notable effect and effective.

TABLE 17

Analysis of Bu-Nao-Gao effect for cerebral palsy of different severities (78 cases)

|  | cured | notable effect | effective | no effect | total effective (%) |
| --- | --- | --- | --- | --- | --- |
| mild | 2 |  | 6 | 1 | 8/9 (88.9%) |
| moderate | 5 | 9 | 25 | 3 | 39/42 (92.9%) |
| severe |  | 10 |  | 14 | 24/24 (100%) |
| most severe |  | 2 |  | 1 | 3/3 (100%) |
| % of total | 7/78 (8.97%) | 21/78 (26.9%) | 46/78 (59%) | 4/78 (5.1%) | 74/78 (94.9%) |

TABLE 18

Analysis of Nao-Fu-Kang effect (control) for cerebral palsy of different severities (24 cases)

|  | cured | notable effect | effective | no effect | total effective (%) |
| --- | --- | --- | --- | --- | --- |
| Mild |  | 1 | 3 | 7 | 4/11 (36.4%) |
| moderate |  |  | 1 | 9 | 1/10 (10%) |
| severe |  |  |  | 3 | 0/3 (0) |
| most severe |  |  |  |  | 0 (0) |
| % of total | 0 | 1/24 (4.17%) | 4/24 (16.7) | 19/24 (79.2%) | 5/24 (20.8%) |

2.5 Clinical Follow-Up 60 of 78 cases in the Bu-Nao-Gao group were followed up for a period of 3 months to 4 years, all patients were found in stable conditions or had shown continued improvement. No single case of deterioration was reported.

2.6 Conclusion and Remarks

For the treatment of children cerebral palsy using Bu-Nao-Gao: The rate for notable effective plus cured is significantly higher in Bu-Nao-Gao group (35.9%) than that of the control group (4.2%), P<0.005.

The total effective rate of the Bu-Nao-Gao group (98.9%) is significantly higher than that of the control group (20.8%), P<0.005.

For mild type of cerebral palsy, the total effective rate of the Bu-Nao-Gao group (88.9%) is significantly higher than that of the control group (36.4%), P<0.01.

For moderate type of cerebral palsy, the total effective rate of the Bu-Nao-Gao group (92.9%) is significantly higher than that of the control group (10%), P<0.005.

For severe type of cerebral palsy, all of the 24 cases in Bu-Nao-Gao group (100%) showed effective results, and none of the 3 cases in the control group showed any effect.

For most severe type of cerebral palsy, all three cases treated by Bu-Nao-Gao gained effective results, and no patient of this severity was included in the control group.

Therefore Bu-Nao-Gao was found to have significant therapeutic effect on cerebral palsy.

Clinical Study #3. Bu-Nao-Gao in the Treatment of Paralysis as a Result of Head Trauma (a Trial of 66 Cases)(38)

3.1 General Information

This clinical trial was carried out between January 1989 to December 1992 by the provincial hospital of Chinese Medicine, Lanzhou, GanSu province. The details are listed in Table 19.

TABLE 19

General information about patients with paralysis resulting from head trauma in Bu-Nao-Gao group and control group

|  | Bu-Nao-Gao group | Control group |
|---|---|---|
| Total cases | 46 | 20 |
| Male: | 34 | 15 |
| Female: | 12 | 5 |
| In-patients | 34 | 20 |
| Outpatients | 12 | |
| Range in Age | 1.5 to 71 yrs (average 29 yrs) | 8 to 50 yrs (average 32 yrs) |
| 0–9 yrs | 6 | 1 |
| 10–17 yrs | 2 | 5 |
| 18–29 yrs | 16 | 0 |
| 30–39 yrs | 8 | 6 |
| 40–59 yrs | 12 | 8 |
| >60 yrs | 2 | 0 |
| Disease Severity | | |
| Mild ($III^+$–$V^-$)* | 12 | 8 |
| Moderate ($II^+$–III) | 17 | 4 |
| Severe ($I^+$–II) | 10 | 3 |
| Very severe (0–I) | 7 | 5 |
| Duration of illness | | |
| <1 month | 3 | 0 |
| 1–3 months | 8 | 4 |
| 3–6 months | 5 | 2 |
| 6–12 months | 10 | 3 |
| 1–3 years | 13 | 11 |
| 3–5 years | 5 | 0 |
| 5–10 years | 1 | |
| 15 years | 1 | |
| Cause of injuries | | |
| Car accident | 20 | 2 |
| Bicycle accident | 3 | |
| Motorcycle accident | 1 | 2 |
| Fall from high places | 4 | 1 |
| Fall from flat ground | 5 | |
| Manslaughter | 9 | 1 |
| Heavy object struck | 2 | 14 |
| surgery | 1 | |
| Complications | | |
| Headache | 33 | 9 |
| Dizziness | 31 | 8 |
| Aphasia | 11 | 2 |
| Dysphasia | 15 | 7 |
| Dysphagia | 7 | 3 |
| Sleepiness | 5 | 2 |
| Slow responsiveness | 11 | 3 |
| mentally retarded | 12 | |
| Decerebral rigidity | 4 | |
| vegetative states | 3 | |
| lack of bladder and bowl control | 13 | 5 |
| optic nerve atrophy | 1 | 3 |
| blurred vision | 3 | |
| facial nerve paralysis | 3 | 1 |
| epilepsy | 7 | 3 |
| multiple cranial nerve injury | 1 | 1 |
| Brain CT scan | 33 tested | 7 tested |
| normal | 7 | 1 |
| localized region of reduced density | 12 | 4 |
| localized region of high density | 3 | |
| Intracranial hematoma | 3 | 6 |
| Epidural hematoma | 4 | 1 |
| Subdural hematoma | 1 | |
| Subdural fluid | 3 | |
| Hydrocephalus | 2 | |
| Brain atrophy | 3 | |
| Brain infarct | 2 | |
| Skull fracture | 14 | |
| Electroencephalography (EEG) | 40 tested | 6 tested |
| Normal: | 5 | |
| Slightly abnormal: | 14 | 1 |
| Moderately abnormal: | 16 | 1 |
| Severely abnormal: | 5 | 4 |
| Diagnosis | | |
| Brain laceration | 29 | 12 |
| Brain laceration combined with skull base fracture | 1 | |
| Intracranial hematoma | 8 | 7 |
| Chronic intracranial hematoma | 1 | |
| Epidural hematoma | 4 | |
| Subdural hematoma | | 1 |
| Brain stem injury (vegetative state) | 3 | |
| Lingual diagnosis | | |
| Substance of tongue | | |
| pinkish (Dan Hong) | 8 | 5 |
| red (Hong) | 16 | 9 |
| dark red (Hong An) | 8 | 3 |
| plain (Dan) | 12 | 2 |
| dark plain (Dan An) | 2 | 1 |
| Tongue coating | | |
| Thin white coating (Bo Bai) | 8 | 12 |
| white coating (Bai) | 22 | 2 |
| white glossy coating (Bai Ni) | 5 | 2 |
| yellow coating (Huang) | 7 | 3 |
| yellow glossy coating (Huang Ni) | 3 | 3 |
| little coating (shao tai) | 1 | |
| Pulse | | |
| fine pulse (Xi Mai) | 24 | |
| stringy pulse (Xuan Mai) | 13 | 8 |
| stringy large pulse (Xuan Da Mai) | 1 | |
| stringy fine pulse (Xuan Xi Mai) | | 3 |
| rapid pulse (Shu Mai) | 1 | |
| Slippery pulse (Hua Mai) | 5 | |
| Deep slow pulse (Chen Huan Mai) | 2 | |
| Deep stringy pulse (Chen Xuan Mai) | | 2 |
| Fine rapid pulse (Xi Mai) | | 1 |
| Deep fine pulse (Chen Xi Mai) | | 6 |

TABLE 20

Treatment Strategy for Bu-Nao-Gao & control groups for paralysis by head trauma

|  | Bu-Nao-Gao Oral intake of Bu-Nao-Gao alone No additional training or other medications | Control Combined treatment of Chinese & Western medicines, acupuncture, physical therapy |
|---|---|---|
| Total cases | 46 | 20 |
| Hospitalized | 34 | 20 |
| Out-patients | 12 | |
| Dosage | 2 cubes/day | |
| Duration of treatment | | |
| 1 month | 10 | 4 |
| 2 months | 16 | 3 |
| 3 months | 6 | 2 |
| >3 months | 14 | 11 |

3.2 Criteria for Clinical Evaluation (the Internationally Used Six-Grade Criteria)

Cured: movement became normal, muscle strength reached to grade V

Notable effect: muscle strength improved over 2 grade.

Effective: muscle strength improved over 1 grade.

No effect: muscle strength improved less than 1 grade.

3.3 Results

TABLE 21

Therapeutic efficacy of Bu-Nao-Gao for paralysis after head trauma

| Effect | Bu-Nao-Gao (%) | Control (%) |
|---|---|---|
| Total | 46 | 20 |
| Cured | 7 (15%) | 0 |
| Notable | 15 (33%) | 3 (15%) |
| Effective | 21 (46%) | 5 (25%) |
| No effect | 3 (6%) | 12 (60%) |
| Total effective | 43 (93%) | 8 (40%) |

TABLE 22

Total effective rate of Bu-Nao-Gao and control groups for paralysis of different severities

| Severity | Total effective rate | |
|---|---|---|
| | Bu-Nao-Gao | Control |
| Total | 46 | 20 |
| Mild (III$^+$–V$^-$) | 10/12 (83%) | 3/8 (37.5%) |
| moderate (II$^+$–III) | 16/17 (94.1%) | 2/4 (50%) |
| severe (I$^+$–II) | 10/10 (100%) | 3/3 (100%) |
| most severe (0–I) | 7/7 (100%) | 0/5 (0) |
| Total effective | 43/46 (93.4%) | 8/20 (40%) |

3.4. Conclusion and Remarks

For the treatment of paralysis after head trauma using Bu-Nao-Gao: The total effective rate of the Bu-Nao-Gao group (93%) is significantly higher than that of the control group (40%). P<0.005.

The rate for notable effective plus cured is significantly higher in Bu-Nao-Gao group (47.8%) than that of the control group (15%). P<0.025.

Therapeutic efficacy for other neuropsychological symptoms: Three patients in vegetative state regained consciousness, and one patient can move around easily. With the exception of no improvement for two cases of aphasia, and two cases of dysphasia, all other symptoms are either cured or notably improved.

Clinical Study #4: Bu-Nao-Gao in the Treatment of 23 Patients of Motor Neuron Disease (39)

4.1. General Information

This clinical trial was carried out between January, 1989 and December, 1992 by the provincial hospital of Chinese Medicine, Lanzhou, GanSu province.

Total cases: 23 cases 20 cases hospitalized, 3 cases outpatient

Age: Range 24 to 68 years of age (average 44 years)

4 cases (20–29 years of age), 2 cases (30–39 years of age), 7 cases (40–49 years of age), 8 cases (50–59 years of age), 2 cases (over 60 years of age).

Stage of Progression:

2 cases mild (muscle strength grade III$^+$~V$^-$, no bulbar syndromes).

8 cases moderate (muscle strength grade II$^+$~III, no bulbar syndromes.

13 cases Severe (muscle strength grade 0~II or with bulbar syndromes.

TABLE 23

Analysis of Bu-Nao-Gao effect on paralysis of different severities (46 cases)

| | Cured | Notable effect | Effective | No effect | Total effective (%) |
|---|---|---|---|---|---|
| mild (III$^+$–V$^-$) | 6 | | 4 | 2 | 10/12 (83.3%) |
| moderate (II$^+$–III) | | 2 | 14 | 1 | 16/17 (94.1%) |
| severe (I$^+$–II) | | 7 | 3 | | 10/10 (100%) |
| most severe (0–I) | 1 | 6 | | | 7/7 (100%) |
| % of Total | 7 (15.2%) | 15 (32.6%) | 21 (45.6%) | 3 (6.5%) | 43/46 (93.4%) |

TABLE 24

Analysis of the control group effect on paralysis of different severities (20 cases)

| | Cured | Notable effect | Effective | No effect | total effective (%) |
|---|---|---|---|---|---|
| Mild (III$^+$–V$^-$) | | | 3 | 5 | 3/8 (37.5%) |
| moderate (II$^+$–III) | | | 2 | 2 | 2/4 (50%) |
| severe (I$^+$–II) | | 3 | | | 3/3 (100%) |
| most severe (0–I) | | | | 5 | 0/5 (0) |
| % of Total | 0 | 3 (15%) | 5 (25%) | 12 (60%) | 8/20 (40%) |

11 out of the 23 patients had bulbar syndromes. Most cases had been treated elsewhere before being included in the Bu-Nao-Gao trial.

| Duration of illness: | |
| --- | --- |
| 4 cases | <1 year |
| 9 cases | 1–3 years |
| 4 cases | 3–5 years |
| 3 cases | 5–7 years |
| 2 cases | 7–10 years, |
| 1 case | >10 years. |

EMG: 20 cases were tested for EMG, and all suggested damage of neuronal origin.

Clinical Diagnosis:
  Amyotrophic lateral sclerosis: 13 cases
    7 cases without bulbar syndromes,
    6 cases with bulbar syndromes.
  Primary lateral sclerosis: 8 cases
    4 cases without bulbar syndromes,
    4 cases with bulbar syndromes.
  Progressive muscular atrophy: 2 cases
    1 case without bulbar syndromes,
    1 case with bulbar syndromes.

Complications and Concomitant Conditions:
  3 cases with coronary heart disease,
  1 case with cerebral infarct,
  1 case with hepatitis B,
  4 cases with lung infection,
  1 case with respiratory palsy.

ECG:
  20 cases tested
  10 cases normal,
  4 cases with insufficient coronary blood supply,
  3 cases right heart enlargement
  1 case incomplete right-bundle block
  2 cases incomplete left-bundle block (frontal branch)

Lingual diagnosis: (a Diagnostic Technique by Observing the Texture, Color and Moisture of the Coating and the Substance of the Tongue)
  Substance of Tongue:
  4 cases pinkish (Dan Hong);
  4 cases red (Hong);
  3 cases dark red (Hong An);
  6 cases dark plain (Dan An);
  6 cases plain (Dan);
  Tongue Coating:
  16 cases white coating (Bai);
  1 case white glossy coating (Bai Ni);
  3 cases yellow coating (Huang);
  3 cases yellow glossy coating (Huang Ni).

Pulse:
  16 cases fine pulse (Xi Mai)
  6 cases stringy pulse (Xuan Mai)
  1 case rapid pulse (Shu Mai)

4.2 Treatment Strategy

Bu-Nao-Gao alone, taken orally 2 cubes/day.

As for all the other clinical and experimental studies, the Example 1 formulation (listed in the example section) was used (at a 273 g raw material/day dosage) for this study.
7 cases—finished 30-day treatment
5 cases—finished 60-day treatment
4 cases—finished 90-day treatment
7 cases—finished over 90-day treatment Due to the often fast-deteriating nature of this disease and the ethical issues involved, no control group was set up for this study.

4.3 Criteria for Therapeutic Efficacy

Due to the already well-established course of development for this disease, efficacy of the treatment is evaluated based on patients' pre-treatment conditions and the trend of deterioration.

1) Clinically cured: disappearance of bulbar palsy, muscle strength improved to grade V.
2) Notable effect: bulbar palsy significantly improved, muscle strength improved more than 2 grade.
3) Effective: bulbar palsy improved, muscle strength improved more than 1 grade.
4) No effect: bulbar palsy continue to exist, no improvement of muscle strength or improvement was less than 1 grade.
5) Deteriorated: continuous deterioration of symptoms or death.

4.4 Results (Table 25)

TABLE 25

Therapeutic efficacy of Bu-Nao-Gao on motor-neuron diseases (23 cases)

| | mild | moderate | severe |
| --- | --- | --- | --- |
| Total | 2 | 8 | 13 |
| cured | | 1 | |
| notable | | 3 | 2 |
| effective | 2 | 3 | 8 |
| no effect | | 1 | 2 |
| deteriorated | | | 1 |
| total effective | 2/2 | 7/8 | 10/13 |

In this study, to the one ALS patient who died during the period of our evaluation, a 3-cubes/day dosage was used at the late stage in an effort to get his conditions under control, and some positive effects were observed even at the very late stage. This patient had been repeatedly treated by Bu-Nao-Gao during the 8-year period after the initial diagnosis, and he made improvements in prior episodes of Bu-Nao-Gao treatment. This patient belonged to the fast-deteriorating type. According to the inventor's experience, if untreated, this patient's natural course of disease may be 2–3 years. This patient appeared to have a family history of similar disorders.

In our experience, the 2-cubes/day dosage was adequate for most patients. When this dosage failed to get the condition under control, a 3-cubes/day dosage (1.5 times of the daily dosage) was used. As soon as the patient's condition was stabilized, the dosage was reduced to the usual 2-cubes/day dosage. Although no side effect had been seen with the 3-cubes/day dosage, patients were not advised to go on this high dosage unnecessarily.

4.5. Strategy for Longer-Term Treatment

After the clinical evaluation during the stated periods, patients were discharged from the hospital when considered clinically safe. Most patients took 0.5–1 year's supply of Bu-Nao-Gao for continued treatment as outpatients.

Every three-month treatment was considered as one cycle. Patients were advised to take a one-week break after each three-month cycle to avoid any potential side effects (on the condition that the disease was in a reasonably stable condition). After taking Bu-Nao-Gao for 3–6 months, if the disease showed no sign of comeback after Bu-Nao-Gao was stopped, these patients could stop taking Bu-Nao-Gao. However, patients were advised to be back on Bu-Nao-Gao immediately as soon as there was a concern (or any signs) suggesting a comeback of the disease.

Some patients remained stable for many years without continuously taking Bu-Nao-Gao; some patients had to be back on Bu-Nao-Gao for more cycles of treatment when the problems resurfaced. Due to the lack of an effective follow-up mechanism for this disease in our system, long-term follow-up data is not yet available, and this information may become available at a later date.

All patients were advised to avoid stressful situations of all kinds, physical exercise was not recommended for muscle strengthening in this disease.

4.6. Examples of Typical Cases

In addition to the above-summarized report, the following cases reports gave more detailed description of changes in patients with this type of disease.

Case #1 (Amyotrophic Lateral Sclerosis) (40)

Patient: A 50-year-old female (Administration number #69834). Progressive upper limbs weakness for approximately 9 months, was admitted to the hospital on Sep. 18, 1992 with the diagnosis of amyotrophic lateral sclerosis (ALS). The patient begun feeling upper limb weakness without any known reason, later experienced difficulty of raising arms and were unable to unbutton her clothes, and also felt weakness on both lower limbs. EMG (done at other hospital): muscle abnormality of neuronal origin, all nerves tested showed abnormalities of different extents; Diagnosis by other hospital: amyotrophic lateral sclerosis (ALS); After failed all other regular treatments of both Chinese and Western Medicines, and with a progressively worsening condition, the patient was admitted to our hospital. Upon hospitalization: the patient showed weakness of all four limbs, could not raise her upper limbs above shoulder, both hands could not do gripping and stretching, could not unbutton her clothes, difficulty of lifting her feets while walking with a feeling of rigidity, could only go up and down stairs by holding onto railing, could see muscle jumping all over her body.

Tonque: pink red, with a thin white coat, fine pulse.

Physical exam: Cranial nerves (normal); obvious atrophy of thenar muscles interosseous muscles and forearm muscles and fasciculation, and muscle strength $III^-$; no muscle atrophy in the lower limbs, and muscle strength $III^+$; muscle tone of four limbs (low); reflexs of ankel-jerk, Biceps-jerk, Triceps-jerk and Knee-jerk are all hyperactive; Unable to induce pathological reflexes. No abnormalities of bladder control and bowel movement; No abnormality in sensory. Diagnosis according to Western Medicine: amyotrophic lateral sclerosis (ALS). Diagnosis according to Chinese Medicine: Wei Zheng (belong to insufficiencies of liver and kidney, and insufficiencies of Qi and blood), therefore the treatment strategy require nourishment of liver, kidney, Qi and blood. Treatment given: Bu-Nao-Gao (two cubes/day) alone. Two weeks after Bu-Nao-Gao: increased muscle strength in four limbs, could raise upper limbs above head but could not stretch straight; reduced rigidity in the lower limbs and reduced muscle jumping in whole body. One month after Bu-Nao-Gao: could raise upper limbs above should and could stretch straight, could do up and down stairs more freely than before. Two months after Bu-Nao-Gao, all five fingers of both hands could stretch out and could unbutton clothes, could go up and down stairs easily, muscle strength $III^+$–$V^-$. After being considered to have made an notable improvement, the patient was discharged from the hospital.

Case #2 (Amyotrophic Lateral Sclerosis) (40)

Patient: A 25-year-old male (Administration number #73819). Weakness of four limbs for approximately one year, was admitted to the hospital on Aug. 7, 1993 with the diagnosis of amyotrophic lateral sclerosis (ALS). Upon hospitalization: the patient showed weakness of all four limbs, weak gripping (only 5 Kg), obvious muscle atrophy of four limbs and both hands, twitching of both both upper limbs, unsteady walking (could only manage 100 meters), difficulty of walking up and down stairs. Tonque: red, with white coat, fine pulse. Physical exam: Lung and heart (–), muscle strength of four limbs (grade III), muscle tone (normal), tendon reflex (hyperactive), Babinski sign on both sides (+), Hoffmann sign on both sides (+); EMG: injury of neuronal origin. Diagnosis according to Chinese Medicine: Wei Zheng (liver and kidney weakness); Diagnosis according to Western Medicine: amyotrophic lateral sclerosis (ALS). Treatment strategy: Bu-Nao-Gao (two cubes/day) alone. 20 days after Bu-Nao-Gao: slightly enriched muscle volume, walking more steadily than before, gripping of both hands increased from 5 Kg to 20 Kg, could walk by himself for 2–3 hours, could walk up and down stairs by himself rather easily, muscle strength of four limbs V–. After one-month treatment with Bu-Nao-Gao, significant improvement was observed and the patient was discharged.

Case #3 (Primary Lateral Sclerosis) (26)

Patient: A 51-year-old male with a 6-month history of weakness in four limbs and lower limb rigidity, and was diagnosed by neurologists of other hospitals as "lateral sclerosis". His symptoms worsened continuously despite all the treatments with both Chinese and Western medicines before being admitted to our hospital.

Diagnosis: Primary lateral sclerosis.

After treatment with a decoction modified from "Fu Shou San", the patient showed improved in muscle strength after 15 day's treatment, and can climb stairs without the need for aid (still had difficulty of going downstairs) after 20 day's treatment; he can walk freely (still with some weakness) after 35 day's treatment. After 80 day's treatment, the patient's muscle strength reach grade V (still slight weakness), could walk up and down stairs easily and had normal gait. His pathological reflexes disappeared, and physiological reflexes of four limbs were only slightly active.

This patient was treated with a decoction when the cube form of Bu-Nao-Gao (or the consensus formulation) was not yet invented, nevertheless this report reflected one of the early attempts by the inventor to define a therapeutic rule (or consensus formulation) for treating this type of disease.

4.7. Potential Side Effects

Due to the rather rapidly deteriorating nature of motor neuron disease (particularly ALS), and the potential of a long-term repeated use of Bu-Nao-Gao for these patients, the following advice and precautions were given to patients: This formulation was designed to be used alone without anticipating further combination with other drugs or supplements without proper medical supervision. Furthermore, people with certain medical conditions may put themselves at risk by using this formulation: i.e. (a) people with hypertension with blood pressure above 150/90 mmHg may put themselves at risk by taking this formulation without first lowing their blood pressure to a clinically safe level; (b) people with problems with blood clotting (i.e. bleeding tendency) may put themselves at risk by taking this formulation due to the anti-coagulating effect of this formulation; (c) Women in pregnancy or lactation should not use this formulation.

The only known side-effect of this formulation in people with suitable medical conditions (according to the experience of more than 25 years) has been an increased bowel movement, a problem which will usually resolve by itself within the first one or two weeks' usage. Despite the anti-coagulation effect of the formulation, no bleeding tendency has so far been reported from our long-term experience. For longer-term usage, a one-week break after every three-months usage is recommended.

4.8 Conclusion

Most patients treated by Bu-Nao-Gao has failed conventional treatment elsewhere (both Chinese and Western medicines). Bu-Nao-Gao has shown to be effective for treating motor-neuron disease with a total effective rate of 82.61% during the period of our evaluation. During the follow-up period (though incomplete), some patients (including some ALS patients) remained stable for many years without continuously using Bu-Nao-Gao; Some other ALS patients experienced the comeback of the disease several times. In every occasion of the disease comeback, Bu-Nao-Gao had demonstrated its beneficial effect on slowing the disease progression.

Bu-Nao-Gao has Been Shown in the Inventor's Experience to Have a Significant Slowing-Down Effect on This Dreadful Disease—a Disease Our Humanity has so Far no Effective Means to Stop.

Clinical Study #5: Treatment of Patients in Vegetative State (Total Four Cases) (12,42)

Patient #1: An 18-year-old female, in a vegetative state for 10 months after initial head injury. After taking Bu-Nao-Gao (cube form) for 10 days, she appeared to be in a slightly conscious state and to be able to recognize people; on the 15$^{th}$ day, she was able to swallow food and feeding tube was removed; on 20$^{th}$ day, she was able to speak simple words and could recognize her parents, had some improvement on limb muscle strength (strength grade I); Two months after Bu-Nao-Gao, she showed continued improvement on consciousness and intelligence (could remember her date of birth, could call out the names of her classmate, could tell Dr. Xia that "Uncle Xia, I have lost my intelligence", could translate a few English words into Chinese), etc (note: this is only a partial translation) (42).

Patient #2: A 17-year-old female, in a vegetative state for 6 month after brain surgery.

Diagnosis: Injury to cerebral and brain stem, coma, de-celebral rigidity (vegetative state).

14 days after taking Bu-Nao-Gao, she appeared to be in a slightly conscious state and to be able to recognize objects; 20 days after taking Bu-Nao-Gao, she could answer yes or no with her eyes and could express her emotions; one month after taking Bu-Nao-Gao, she regained a clear consciousness, muscle strength had improved with decreased rigidity; Two month after taking Bu-Nao-Gao, she could speak simple sentences; 70 days after taking Bu-Nao-Gao, she could sit up, turn her neck, muscle strength in four limbs (I–III), reduced muscle rigidity, and decerebrate rigidity was relieved.

(Note: this is only a partial translation) (42).

Patient #3: An 8-year-old girl with a three-month history of paralysis and in vegetative state (post encephalitis). Three month prior, the patient was admitted to a hospital due to a high fever followed by a state of coma, and was diagnosed as type B encephalitis. Both CT and EEG revealed widespread damage and abnormality of cerebral cortex. After various emergency treatments, she remained to be in a state of dementia, quadriplegia, tracheotomy, opisthotonus, a vegetative state. After treatment with a decoction of Chinese Medicine (with constant modifications) for 15 days, she started to show clinical improvements; after 30 days treatment, she made significant improvements (i.e. could speak simple words, muscle strength improved, etc.); After 60 days treatment, her intelligence was close to normal, could speak normally. After another month of treatment using the decoction at a reduced dosage (every other day treatment), she had a complete recovery (12). 6 years later (at age of 14 years), the patient came back for a follow-up. She was completely normal, and was an outstanding student in her class (middle school) (note: this follow-up result was not in the original publication, was documented in the patient's record in the hospital).

Case #4: for 6 months after cerebellar operation. Details can be entered later on.

Clinical Study #6: Treatment of Oliverpontocerebellar Atrophy (Dejerine-Thomas Type, 3 Cases) (43)

There are two types of Oliverpontocerebellar atrophy: hereditary (Menzel type) and sporadic (Dejerine-Thomas type). All three cases treated here belong to the latter and had failed long-term conventional treatment elsewhere (both Western and Chinese Medicines). The followings are reports of the three cases.

Treatment strategy: Oral intake of Bu-Nao-Gao, 2 cubes/day.

No additional medication was used.

Case #1: 40-year-old male with a 4-year history. Notable effect was achieved after 100 day's treatment.

Case #2: 47-year-old male with a 2-year history. Notable effect was achieved after 120 day's treatment.

Case #3: 60-year-old female with a 3-year history. Notable effect was achieved after 30 day's treatment.

Clinical Study #7. Treatment of Hereditary Cerebellar Ataxia (3 Cases) (44)

All three cases treated have failed long-term conventional treatment elsewhere (both Western and Chinese Medicines).

Treatment strategy: Oral intake of Bu-Nao-Gao, 2 cubes/day. No additional medication was used.

Case #1: 23-year-old male with two-year history. Notable effect was achieved after 30 day's treatment.

Case #2: 48-year-old Female with five-year history. Notable effect was achieved after 60 day's treatment.

Case #3: 75-year-old male with one-year history. Notable effect was achieved after 30 day's treatment.

Clinical Study #8. Treatment of Dementia

More than twenty patients (mainly as outpatients) with senile dementia were treated with Bu-Nao-Gao. Significant improvements have been observed in many of these patients, detailed information will become available later on.

Many patients treated in the study for sequel of stroke and head injury also had dementia (22, 38).

Clinical Study #9: Treatment of 52 Patients with Sequel of Apoplexy with Fe-Shou-Yi-Qi-Ho-Xie" Decoction for (22).

Satisfactory therapeutic efficacy was observed with this self-designed decoction and its various modifications used. The decoctions reported here lacked one of the core ingredients in the currently applied formulation—"the Bu-Nao-Gao" formulation. And many components which were not used in "the Bu-Nao-Gao" formulation were also added.

This study reflected one of the early attempts by the inventor to define a therapeutic rule (or consensus formulation) for treating this type of disease.

Other case reports using similar principle had demonstrated satisfactory results (20–21, 27).

The currently applied formulation—"the Bu-Nao-Gao" formulation have all the key ingredient for achieving above clinical effect, also based on the inventor's experience of using Bu-Nao-Gao (cube form or decoction) in some patients with similar conditions, the currently applied formulation is therefore considered potentially as effective as the decoction reported for treating this type of conditions.

Clinical Study #10: Treatment of 50 Patients of Apoplexy Combined with Pseudo-Bulbar Palsy (27).
Dysphasia (Gou Yin Bu Quan):
Total effective rate 98% (notable effect 58%)
Dysphagia (Tuen Yian Kun Nan) and choking:
Total effective rate 98% (notable effect 94%)

The decoction reported here lacked one of the core ingredients in the currently applied formulation- "the Bu-Nao-Gao" formulation. And additional components which were not used in "the Bu-Nao-Gao" formulation were also added. This study reflected one of the early attempts by the inventor to define a therapeutic rule (or consensus formulation) for treating this type of disease.

The currently applied formulation- "the Bu-Nao-Gao" formulation have all the key ingredient for achieving above clinical effect, and is therefore expected to be potentially as effective as the decoction reported (if not better).

Clinical Study #11. Treatment of Encephalopathy

Case #1: sequel of toxic encephalopathy (five months) (46) Patient: A 5-year-old boy (administration #71928) Dementia, aphasia, could not stand or walk, very low intelligence (DQ=13). After hospitalization, he was treated with Bu-Nao-Gao (one cube/day). 10 days after treatment, he was able to walk with just a little assistance by others; 1 month later, he could walk by himself for 1–2 steps, could say "mum"; 2 month later, he could walk more steadily, and could walk for five meters on his own, muscle strength of both lower limbs IV$^+$. He was considered to have made a notable improvement and was discharged from the hospital.

Case #2: Delayed encephalopathy caused by carbon monoxide poisoning (1 month) (details of this case is kept in the hospital's record)

Patient: A 63-year-old male with a prior history of carbon-monoxide poisoning for one month. He was in a state of coma with frequent convulsion of extremities; EEG showed severe abnormality and CT revealed brain atrophy. After Bu-Nao-Gao (2 cubes/day) treatment for 2 weeks, he regained consciousness, and could recognize people, but still had aphasia; One month after Bu-Nao-Gao, he could speak simple words; 2 months after Bu-Nao-Gao, he could walk by himself, also he could speak fluently and answer questions correctly. EEG and brain CT all returned to normal.

Clinical Study #12. Treatment of Multiple Sclerosis (MS)

More than three cases of patients with multiple sclerosis have been treated. More complete information regarding these patients will be entered at a later stage.

Case #1: A 50-year-old male patient with a 2-year history, and worsening condition for two months (15).

Significant clinical improvement was observed after treatment for 30–35 days using a decoction that bore some resemblance to Bu-Nao-Gao. However, it lacked one of the core ingredient of Bu-Nao-Gao, and many non-Bu-Nao-Gao ingredients were also used at various points. This patient did not have any relapse during the follow-up period of one and half-years. This report reflected one of the early attempts by the inventor to define a therapeutic rule (or consensus formulation) for treating this type of disease.

Case #2. A female outpatient in her early twenties diagnosed with multiple sclerosis by other hospitals (also by the inventor): Within the one year before Bu-Nao-Gao was used, she had 5–6 relapses, and was severely handicapped and was in serious condition. After taking Bu-Nao-Gao (similar to Example 1) alone for two weeks, she started showing significant clinical improvements. She took Bu-Nao-Gao on a daily basis for 2 years, and then on a 2–3-times/week basis. Being followed up by the inventor for the last 8 years, she has not had a single relapse ever since (only one minor fluctuation which may not be qualified as a relapse). Although still feeling weak at times, she was able to resume normal work and normal life (not published).

The currently applied formulation—"the Bu-Nao-Gao" formulation have all the key ingredient for achieving the above clinical effects, also based on the inventor's experience of using Bu-Nao-Gao (cube form or decoction) in some patients with similar conditions, the currently applied formulation is therefore considered potentially as effective as the decoctions used in this type of disease.

Clinical Study #13. Treatment of Myelitis (19, 45).

Case #1: Acute myelitis (45).

Patient: A 37-year-old female, weakness of lower limbs and urine retention for 6 days. The patient had a cold two weeks prior the weakness. Bu-Nao-Gao (the cube/tar form, example 1 of the current application) was given at a 2-cubes/day dosage. On the 6th days of Bu-Nao-Gao treatment, urine retention was resolved, and urethral catheter was removed; On the 10th day after Bu-Nao-Gao, she could walk on flat ground with a cane; on $20^{th}$ day after Bu-Nao-Gao, she could walk freely with a normal gait, and could walk up and down stairs without aid, the muscle strength of four limbs reached grade V, but the painful sensation around waist somewhat remained. She continued to be on Bu-Nao-Gao for another two months, and clinical cure was achieved in this patient.

Case #2: Sequel of neuromyelitis optica (Devic disease, note by the translator) (19).

Patient: A 27-year-old female patient with one-year history. Clinical cure was achieved in this patient after 27 day's treatment using a decoction that bore some resemblance to Bu-Nao-Gao. However, this formulation did not have the consensus of this current Bu-Nao-Gao application, and many additional ingredients were also included at various points.

Although no well-controlled clinical trial was conducted on myelitis of all types, based on the experience and the theory of the inventor, it is predicted that the currently applied formulation should have therapeutic effect on this type of disease.

Clinical Study #14. Treatment of Polyneuritis of All Types (16)

Patient: A 59-year-old male. 6 month's prior, he started experiencing numbness of hands and feet, with a slightly painful sensation. He was afraid of cold and his condition got worse when encountered coldness. He failed other treatments of Western and Chinese Medicines. He had no history of severe illness or drug intake. Examination: in addition to hand and feet numbness, his hands and feet were cold, his whole body was weak. Neurological examination: weakness of hands and feet; slightly lower muscle tone in four limbs; hypoactive tendon reflexes; reduced sensory to pain, touch and temperature below the ½ of all forelimbs;

reduced sensory to sound at angles and wrist. Diagnosis: polyneuritis. Clinical cure was achieved after a one-month treatment with decoctions of Chinese medicine.

Decoctions used for this patient at various points eventually had used all ingredients comprised in the current Bu-Nao-Gao formula, and many non-Bu-Nao-Gao ingredients were also used.

Although the decoction used for this patient was not the same as the formulation in application, based on the experience and the theory of the inventor, it is predicted that the currently applied formulation should have a beneficial effect on this disease as well as all other types of polyneuritis.

Clinical Study #15. Treatment of Muscle-Stiffness (28)

Patient: A 44-year-old female with an apparent 10-year history and worsening of conditions for the past 4–5 years. After treatment with a decoction of Chinese Medicine for 40 forty days, notable effect (close to clinical cure) was observed, and no re-occurrence of symptoms was observed during the half-year follow-up period. The decoction reported here lacked two of the core ingredients in the currently applied formulation—"the Bu-Nao-Gao" formulation. And many components which were not used in "the Bu-Nao-Gao" formulation were also tested therefore made the consensus formulation not obvious.

Although the decoction used for this patient was not the same as the formulation in application, based on the experience and the theory of the inventor, it is predicted that the currently applied formulation should have a beneficial effect on this disease as well as all other types of muscle stiffness.

Clinical Study #16. Treatment of Muscle Spasm (29)

Patient: A 50-year-old male with a 4-year history of gastrocnemius muscle spasm, 2–3 times every night. At each onset, both legs were very tight, the spasm often led to a global shape of hardness with severe pain. Each onset last 2–5 minutes. The patient endured great suffering, and had gone through all types of Chinese and western medicine treatments (including acupuncture, massage, physical therapies). Physical exam did not reveal obvious abnormality. After treatment of a decoction of Chinese Medicine (with continuous modifications according to patient's response) for 6 days, the frequency of spasm was greatly reduced; After another 10 day's continued treatment, no more onset occurred. No re-occurrence was reported during the half-year follow-up. This patient was considered cured of the disease.

The decoction reported here lacked two of the core ingredients in the currently applied formulation—"the Bu-Nao-Gao" formulation, and many components which were not used in "the Bu-Nao-Gao" formulation were also tested. However, based on the experience and the theory of the inventor, it is predicted that the currently applied formulation should have a similar strength needed for achieving the above effect.

Clinical Study #17. Treatment of Giant-Cell Arteritis (47)

A self-designed "Fu-Shou-Yi-Qi-Huo-Xie" decoction was used for treating three patients with giant cell arteritis. The three patients were a 29-year old male with a 2-year history, a 20-year-old female and a 42-year-old male. Clinical cure was achieved in all three patients after 20–60 day's treatment. After 1–3 year follow-up, no relapse was reported in all three patients.

The decoction reported here lacked one of the core ingredients in the currently applied formulation—"the Bu-Nao-Gao" formulation. And many components which were not used in "the Bu-Nao-Gao" formulation were also tested.

Although the decoctions used for these patient were not the same as the formulation in application, based on the experience and the theory of the inventor, it is predicted that the currently applied formulation should have a beneficial effect on this type as well as other types of arteritis.

Note: Due to the current restrains on time and resources, many new clinical data were not yet summarized. These clinical information (both inpatients or outpatients) will either be entered at a later date or be provided upon request.

REFERENCES

1. Xia, YongChao: A patent application (CN 1182603A) for a formulation of Chinese Medicine (also termed Bu-Nao-Gao) has been filed in China and was released on May 27, 1998.

In this patent application, a formulation comprising 14 ingredients was applied, and a patent has been granted for this application.

This current formula application is significantly different from the Chinese patent in the ingredients comprised.

2. Xia, YongChao. "Fo-Shou" therapeutic serie of Chinese Medicine. Modern Chinese Medicine (Xian Dai Zhong Yi). 1989: 2:45.

Also collected in the special issue "Bu-Nao-Gao in the treatment of brain damage and children feeblemindedness" through internal distribution by the Provincial Hospital of Chinese Medicine, Lanzhou, GanSu Province, P. R. China.

3. Xia, YongChao. Modifications of "Finger citron (Fo-Shou) Powder" for the treatment of difficult and complicated diseases. Bright Chinese Medicine (Guang-Ming Zhong Yi) 1991: 2: 26.

4. Xia, YongChao. A two-case report of treating patients with poliomyelitis (bulbar type). GanSu Medicine (GanSu Yi Yiao).1982 (supplement issue): page 42–43.

Clinical cure was achieved in these two cases by using decoctions of Chinese Medicine. The formulation disclosed were significantly modified on the basis of an ancient formula "Bu-Yang-Huan-Wu" decoction.

Formulation described in this report had little similarity with the currently applied "Bu-Nao-Gao" formulation. However, this report reflected one of the many early attempts by the inventor to define a therapeutic rule (or consensus formulation) for treating this type of disease.

5. YongChao Xia. Clinical cure of one patient with post-head-trauma aphasia using a modified "Tong Qiao Huo Xie" decoction. Journal of AnHui Traditional Chinese Medicine (AnHui ZhongYi XueYuan XueBao). 1988, 7 (4): 57.

Patient: 5 year-old boy with aphasia and difficulty of movement for two weeks after the initial head trauma (followed by a state of unconsciousness for three hours). After treatment with a decoction of Chinese Medicine (continuously modified during treatment) for ten days, he regained almost normal speech and gait after this ten-day treatment.

The decoctions described in this paper were completely different from the currently applied formulation—"the Bu-Nao-Gao" formulation, nevertheless this report reflected one of the many early attempts by the inventor to define a therapeutic rule (or consensus formulation) for treating this type of disease.

6. Li, YianYi; YongChao Xia. Clinical cure of one patient with diabetic ocularmotor paralysis. Journal of Traditional Chinese Medicine (Zhong Yi Za Zhi). 1987; 4: 16.

Patient: 61 male. A 10-day's history of double vision and other symptoms of paralysis. Clinical cure was achieved after a two-month treatment using a decoction of Chinese Medicine alone.

The decoction described in this paper lacked some core ingredients comprised by the currently applied formulation—"the Bu-Nao-Gao" formulation. furthermore components which were not used in "the Bu-Nao-Gao" formulation were also tested, therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

7. Xia, YongChao. Clinical cure of one patient with post-traumatic tinnitus. Beijing Journal of Chinese Medicine (Beijing ZhongYi Zazhi). 1988, 6:50.

Patient: a 52-year-old male with a more than 15-year history of post-traumatic tinnitus. After treatment with a decoction of Chinese Medicine for 16 days, significant improvement was observed; His tinnnitus disappeared completely after another two-month treatment.

The decoction described in this paper lacked one of the core ingredients comprised by the currently applied formulation—"the Bu-Nao-Gao" formulation, furthermore, components which were not used in "the Bu-Nao-Gao" formulation were also tested, therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

8. Xia, YongChao. Treatment of one case with severe post-traumatic quadriplegia. ShanXi Journal of Chinese traditional medicine (ShanXi ZhongYi) 1988; 9 (10); 457–458.

Patient: a 20 year-old male with a two-month history of post-traumatic head injury and in a state of coma, and was diagnosed with head injury with skull fracture and brain laceration, quadriplegia. Significant improvement was observed after 40-day's treatment; Almost complete recovery was achieved after 60-day's treatment.

The decoction described in this paper contained all ingredients comprised by the currently applied formulation—"the Bu-Nao-Gao" formulation, however components which were not used in "the Bu-Nao-Gao" formulation were also tested, therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

9. Xia, YongChao. Clinical cure of one patient with spinal arachnoiditis using "Fo-Shou-Yi-Qi-Huo-Xie" decoction and additional herbs. Journal of Gansu College of Traditional Chinese Medicine (GanSu ZhongYi XueYuan Xue-Bao) 1988; 3: 52.

Patient: A 27-year-old male patients with a two-month history.

The decoction described in this paper lacked one of the core ingredients-polygonatum sibiricum (HuangJing) in the currently applied formulation—"the Bu-Nao-Gao" formulation. Furthermore at different time points, components which were not used in "the Bu-Nao-Gao" formulation were also tested, therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

10. Xia, YongChao; Xu, WenKe; Zhang, MinSi. Clinical experience of treating one patient with spinal arachnoiditis. ShanXi Journal of Traditional Chinese Medicine (ShanXi ZhongYi) 1990; 11: 509–510.

Patient: A 43-year-old male patient with a two-year history.

The decoction described in this paper lacked one of the core ingredients-polygonatum sibiricum (HuangJing) in the currently applied formulation—"the Bu-Nao-Gao" formulation. Furthermore at different time points, components which were not used in "the Bu-Nao-Gao" formulation were also tested, therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

11. Xia, YongChao: Clinical cure of one child patient with post-infective brain infarction. JiLin Journal of Traditional Chinese Medicine (JiLin ZhongYi Yao) 1989; 3: 27, Patient: a 4.5-year-old girl with a 4-month history.

The decoction described in this paper was modified from the self-designed "Fo-Shou-Bu-Sui decoction", and have all of the core ingredients of the currently applied formulation—"the Bu-Nao-Gao" formulation. However, at different time points components which were not used in "the Bu-Nao-Gao" formulation were also tested therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

12. Xia, YongChao. Clinical cure of one case with severe paralysis (post-encephalitis type B) using "Fo-Shou-Bu-Sui" decoction. Journal of Chinese Medicine (Zhong Yi Za Zhi) 1989.4: 40.

Patient: an 8-year-old girl with a three-month history of paralysis. Three-month prior, the patient was admitted to a hospital due to a high fever followed by a state of coma, and was diagnosed as type B encephalitis. Both CT and EEG revealed widespread damage and abnormality of cerebral cortex. After various emergency treatments, she remained to be in a state of dementia, quadriplegia, tracheotomy, opisthotonus, a vegetative state. After treatment with a decoction of Chinese Medicine (with constant modifications) for 15 days, she started to show clinical improvements; after 30 days treatment, she made significant improvements (i.e. could speak simple words, muscle strength improved, etc.); After 60 day-treatment, her intelligence was almost normal, could speak normally. After another month of treatment using the decoction at a reduced dosage (every other day treatment), she had a complete recovery.

Six years later (at age of 14 years), she came back for a follow-up. She was completely normal, and was an outstanding student in her class (middle school) (note:

this follow-up result was not in the original publication, was recorded in the patient's record in the hospital).

The decoction described in this paper was modified from the self-designed "Fo-Shou-Bu-Sui decoction", and have all of the core ingredients in the currently applied formulation—"the Bu-Nao-Gao" formulation. However, at different time points components which were not used in "the Bu-Nao-Gao" formulation were also tested, therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

13. Xia, YongChao; Zhou, Jie; Dou, YouYi. One case report of treatment of brachial paralysis (post-injury). XinJiang Journal of Chinese Medicine (XinJiang Zhong Yi Yiao). 1989; 4:–59.

Patient: a 40 year-old female patient with a 20-day history.

Clinical cure was achieved in this patient after 20 day's treatment using a decoction that bore some resemblance to Bu-Nao-Gao. However, many non-Bu-Nao-Gao ingredients) were also added at various points.

The decoction used here did not have the consensus of the currently applied formulation, nevertheless this report reflected one of the many early attempts by the inventor to define a therapeutic rule (or consensus formulation) for treating this type of disease.

14. Han, Yian; Xia, YongChao. Clinical cure of one patient with double vision (diplopia) post-traumatic head injury using "Fo-Shou-Bu-Shui" decoction. GanSu College Journal of Chinese Medicine (GanSu Zhong Yi Xue Yuan Xue Bao) 1989, 2:47.

Patient: 55 year old male with a 20 day's history of head injury. Clinical cure was achieved after almost two-month treatment.

The decoctions used for this patient contained all ingredients comprised in the current Bu-Nao-Gao formula, however many non-Bu-Nao-Gao ingredients were also used. The decoction used here did not have the consensus of the currently applied formulation, nevertheless this report reflected one of the many early attempts by the inventor to define a therapeutic rule (or consensus formulation) for treating this type of disease.

15. Xia, YongChao. Clinical experience of treating one patient with Multiple Sclerosis. Beijing Journal of Chinese Medicine (Beijing Zhong Yi Za Zhi). 1989, 3:41.

Patient: a 50-year-old male patient with a two-year history, and worsening condition for two months. Significant clinical improvement was observed after treatment for 30–35 days using a decoction that bore some resemblance to Bu-Nao-Gao. However, it lacked one of the core ingredients of Bu-Nao-Gao, and many non-Bu-Nao-Gao ingredients were also used at various points. This patient did not have any relapse during the follow-up period of one and half years.

The decoction used here did not have the consensus of the currently applied formulation, nevertheless this report reflected one of the many early attempts by the inventor to define a therapeutic rule (or consensus formulation) for treating this type of disease.

16. Xia, YongChao. Clinical experience of treating one case with peripheral polyneuritis. Si-Chuan Journal of Chinese Medicine (Si-Chuan Zhong Yi). 1989, 6: 37.

Patient: a 59 year-old male with a 6-month's history. Clinical cure was achieved after one-month treatment with a decoction of Chinese Medicine.

Decoctions used for this patient contained all ingredients comprised in the current Bu-Nao-Gao formula, however many non-Bu-Nao-Gao ingredients were also used.

The decoction used here did not have the consensus of the currently applied formulation, nevertheless this report reflected one of the many early attempts by the inventor to define a therapeutic rule (or consensus formulation) for treating this type of disease.

17. Xia, YongChao. Clinical experience of treating sequel of facial nerve paralysis. New Chinese Medicine (Xin ZhongYi). 1990, 11:2.

Patient: a 56 year-old female patient with a ten-month history. Clinical cure was achieved after 15 day's treatment using a decoction that bore some resemblance to Bu-Nao-Gao. However, it lacked one of the core ingredient of Bu-Nao-Gao, and many non-Bu-Nao-Gao ingredients were also used at various points.

The decoction used here did not have the consensus of the currently applied formulation, nevertheless this report reflected one of the many early attempts by the inventor to define a therapeutic rule (or consensus formulation) for treating this type of disease.

18. Li, YianYi and Xia, YongChao. Clinical experience of treating one patient with sequel of facial-nerve paralysis. Journal of GanSu college of Tradional Chinese Medicine (GanSu Zhong Xi Xue Yuan Xue Bao). 1991, 8:32.

Patient: a 52 year-old patient with a 2.5 month history and had failed treatment by other Chinese and Western Medicines. Clinical cure was achieved after 60 day's day's treatment using a decoction that lacked one of the core ingredient of Bu-Nao-Gao, and had many non-Bu-Nao-Gao ingredients.

The decoction used here did not have the consensus of the currently applied formulation, nevertheless this report reflected one of the many early attempts by the inventor to define a therapeutic rule (or consensus formulation) for treating this type of disease.

19. Xia, YongChao. Sequel of neuromyelitis optica (Devic disease, note by the translator). SiChuan Journal of Chinese Medicine (SiChuan ZhongYi ZaZhi). 1990; 2: 41.

Patient: a 27 year-old female patient with one year history. Clinical cure was achieved in this patient after 27 day's treatment using a decoction that bore some resemblance to Bu-Nao-Gao. However, this formulation did not have the consensus of this current Bu-Nao-Gao application, and many additional ingredients were also included at various points.

The decoction used here did not have the consensus of the currently applied formulation, nevertheless this report reflected one of the many early attempts by the inventor to define a therapeutic rule (or consensus formulation) for treating this type of disease.

20. Xia, YongChao. Treatment of one patient with post-apoplexy tremor. TianJin Journal of Traditonal Chinese Medicine (TianJin ZhongYi).1990, 6: 12.

Patient: 67 year-old male with a history of thrombolic apoplexy for 6 months. One month after the initial onset, he has tremor in mouth and hands as well as rigidity of movement. Diagnosis: Cerebral thrombosis, Parkinson's syndrome. Clinical cure was achieved after one-month treatment with a decoction of Chinese medicine. The decoction used contained some (but not all) ingredients that were comprised by the current Bu-Nao- Gao application. However, the decoction used did not have the consensus of this current Bu-Nao-Gao application, and many additional non-Bu-Nao-Gao ingredients were also included at various points.

The decoction used here did not have the consensus of the currently applied formulation, nevertheless this report reflected one of the many early attempts by the inventor to define a therapeutic rule (or consensus formulation) for treating this type of disease.

21. Xia, YongChao. Treatment of stroke with an emphasized use on Radix *angelica sinensis*. YunNan College Journal of Chinese Medicine (YunNan ZhongYi XueYuan XueBao) 1990, 13 (1): 29.

Patient: a 53-year-old male patient with a history of stroke five years ago. Significant clinical improvement was observed after treatment for 20 days using a decoction that bore some resemblance to Bu-Nao-Gao. However, it lacked one of the core ingredient of Bu-Nao-Gao, and many non-Bu-Nao-Gao ingredients were also used at various points.

The decoction used here did not have the consensus of the currently applied formulation, nevertheless this report reflected one of the many early attempts by the inventor to define a therapeutic rule (or consensus formulation) for treating this type of disease.

22. Xia, YongChao; Xu, WenKe; Li, YianYi; Han, Yian; Dou, YouYi; Zhu, YaPing; Zhang, MinSi; Lu, ShaoMin; "Fe-Shou-Yi-Qi-Ho-Xie" decoction for the treatment of 52 patients with sequel of apoplexy. Chinese Journal of Integrated Traditional and Western Medicine (Zhong Xi Yi Jie He Zazhi) 1991, 12:736

Satisfactory therapeutic efficacy was observed with this decoction and its various modifications used. The decoctions reported here lacked one of the core ingredients in the currently applied formulation—"the Bu-Nao-Gao" formulation. And many ingredients which were not used in "the Bu-Nao-Gao" formulation were also tested, therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

23. Li, YianYi and Xia, YongChao. Clinical cure of one patient with visual field defect (Post-sporadic-encephalitis) using a modified decoction of "Fo-Shou-San". Journal of Traditional Chinese Medicine (Zhong Yi Za Zhi). 1991, 7:34.

Patient: 52 year-old male with a left eye visual field defect (temporal side) for approximately 4 months. A two month treatment using a herbal decoction lead to the complete recovery of visual field. This decoction contains several ingredients comprised by the current application. However, it lacked one of the core ingredient of Bu-Nao-Gao, and many non-Bu-Nao-Gao ingredients were also used.

The decoction used here did not have the consensus of the currently applied formulation, nevertheless this report reflected one of the many early attempts by the inventor to define a therapeutic rule (or consensus formulation) for treating this type of disease.

24. Xia, YongChao. Case report of one patient at fifth-year post-head-injury sequel. TianJin Journal of Traditional Chinese Medicine (TianJin ZhongYi). 1992; 5, 13.

Patient: 48 year-old male at fifth-year post-head-injury sequel. The immediate diagnosis after head injury: Skull fracture, brain laceration, intracranial hematoma. Notable effect was achieved after three-month treatment with a decoction of Chinese medicine alone. The decoction reported lacked two of the core ingredients in the currently applied formulation—"the Bu-Nao-Gao" formulation. And many components which were not used in "the Bu-Nao-Gao" formulation were also tested therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

25. Xia, YongChao; Li, YianYi. Case report of one patient with nasal leakage of cerebralspinal fluid. LiaoNing Journal of Traditional Chinese Medicine (LiaoNing ZhongYi ZaZhi). 1992; 36. 13.

Patient: 62-year-old male with a history of nasal fluid leakage for 1.5 years, was diagnosed with cerebralspinal fluid leakage and failed non-invasive treatment everywhere. His symptoms were stopped after 40 day' treatment with a decoction of Chinese medicine alone, and the symptoms did not return during our ten-month follow-up. The decoction reported lacked one of the core ingredients in the currently applied formulation—"the Bu-Nao-Gao" formulation. And many components which were not used in "the Bu-Nao-Gao" formulation were also tested therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

26. Xia, YongChao; Li, YianYi. Case report of one patient with primary lateral sclerosis (note: one form of motor neuron disease) New Journal of Traditional Chinese Medicine (Xin ZhongYi). 1992, 24 (6):22.

Patient: 51 year old male with a 6-month history of weakness in four limbs and lower limb rigidity, and was diagnosed by neurologists of other hospitals as "lateral sclerosis". His symptoms worsened continuously despite all the treatments with both Chinese and Western medicines before being admitted to our hospital.

Our diagnosis: Primary lateral sclerosis.

After treatment with a decoction modified from "Fu Shou San", the patient showed improved in muscle strength after 15 day's treatment, and can climb stairs without the need for aid (still had difficulty of going downstairs) after 20 day's treatment; he can walk freely (still with some weakness) after 35 day's treatment. After 80 day's treatment, the patient's muscle strength reach grade V (still slight weakness), can walk up and down stairs easily and had normal gait. His pathological reflexes disappeared, and physiological reflexes of four limbs were only slightly active. The decoction reported here lacked two of the core ingredients in the currently applied formulation—"the Bu-Nao-Gao" formulation (the two core ingredients were only added together with many other ingredients). And many components which were not used in "the Bu-Nao-Gao" formulation were also tested therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

27. Xia, YongChao; Li, YianYi; Han, Yian; Xu, WenKe; Zhu, YaPing; Dou, YouYi; Zhang, MinSi; Lu, ShaoMin; Luo, Ling.

Clinical study of 50 cases of apoplexy combined with pseudo-bulbar palsy. Journal of Traditional Chinese Medicine (ZhongYi ZaZhi) 1993, 4, 227.

Dysphasia (Gou Yin Bu Quan):
Total effective rate 98% (notable effect 58%)
Dysphagia (Tuen Yian Kun Nan) and choking:
Total effective rate 98% (notable effect 94%)
The decoction reported here lacked one of the core ingredients in the currently applied formulation—"the Bu-Nao-Gao" formulation. And many components which were not used in "the Bu-Nao-Gao" formulation were also tested, therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

28. Xia, YongChao. One case report of treating Congenital muscle-stiffness. Zhong Yi Han Shou Tong Xun, 1992, 29.

Patient: 44 year-old female with an apparent 10-year history and worsening of conditions for the past 4–5 years. After treatment with a decoction of Chinese Medicine for 40 forty days, notable effect (close to clinical cure) was observed, and no re-occurrence of symptoms was observed during the half-year follow-up period. The decoction reported here lacked two of the core ingredients in the currently applied formulation—"the Bu-Nao-Gao" formulation. And many components which were not used in "the Bu-Nao-Gao" formulation were also tested therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

29. Xia, YongChao. One case report of stubborn gastrocnemius muscle spasm. GuangMing Chinese Medicine, 1989, 6: 24.

The decoction reported here lacked two of the core ingredients in the currently applied formulation—"the Bu-Nao-Gao" formulation. And many components which were not used in "the Bu-Nao-Gao" formulation were also tested, therefore made the consensus formulation not obvious.

The decoction used here did not have the consensus of the currently applied formulation, nevertheless this report reflected one of the many early attempts by the inventor to define a therapeutic rule (or consensus formulation) for treating this type of disease.

30. Huang, ZhengLiang; Cui, ZhuMei; Yen, Yuan; Suen, QiXiang; Zheng, YunXia; Ma, Jun. Pharmacological study of Bu-Nao-Gao. Journal of Gansu College of Traditional Chinese Medicine (Gansu Zhong Yi Xue Yuan Xue Bao) 1992; 9(2): 27–31, 31. Huang, ZhengLiang et al: Chinese Medicine 1987; 18(4): 22.

32. Xu, ShuYun et al: Pharmacology College Reports (Yao Xue Xue Bao). 1979; 14(7): 443, 33. Xu, ShuYun et al: Methods for pharmacological experiments. Published by People's Health Press. 1983: 944, 34. Yu, He: Clinical immunological techniques. Published by Shanghai Technology press. 1982: 374.

35. Li, YianYi; Han, Yian; Dou, YouYi; Zhu, YaPing; Zhang, MinSi; Lu, ShaoMin; Wu, QuanYen; Hu, MinLi; Yang, YongShen; Yian, XiaoXia; Xia, YongChao. Clinical and experimental studies of the large-dosage usage of Radix angelica sinensis. Journal of applied integration of traditional and western medicine (Shi Yong Zhong Xi Yi Jie He Za Zhi). 1990; 2: 109.

Also Collected in the special issue "Bu-Nao-Gao in the treatment of brain damage and children feeblemindedness" through internal distribution by the Provincial Hospital of Chinese Medicine, LanZhou, GanSu Province, P. R. China.

36. Clinical study of Bu-Nao-Gao in the treatment of children with feeblemindedness
(a trial of 133 cases).
Department of Cardiovascular and nervous system. Provincial Hospital of Chinese Medicine, LanZhou, GanSu Province. P. R. China
Xia, YongChao; Li, YianYi; Han, Yian; Lu, ShaoMin; Yang, YongShen; Xu, WenKe; Dou, YouYi; Zhu, YaPing; Zhang, MinSi; Hu, MinLi; Wu, QuanYen; Yian, XiaoXia; Luo, Ling.
Department of Pediatrics, Provincial Hospital of Chinese Medicine, LanZhou, GanSu Province. P. R. China
Jin, WenMei
Not yet published in any medical journal. Collected in the special issue "Bu-Nao-Gao in the treatment of brain damage and children feeblemindedness" through internal distribution by the Provincial Hospital of Chinese Medicine, LanZhou, GanSu Province, P. R. China.

37. Clinical study of Bu-Nao-Gao in the treatment of children with cerebral palsy (a trial of 102 cases).
Department of Cardiovascular and nervous system. Provincial Hospital of Chinese Medicine, LanZhou, GanSu Province. P. R. China
Xia, YongChao; Li, YianYi; Han, Yian; Yang, YongShen; Lu, ShaoMin; Xu, WenKe; Dou, YouYi; Zhang, MinSi; Zhu, YaPing; Wu, QuanYen; Hu, MinLi; Yian, XiaoXia; Luo, Ling.
Department of Pediatrics, Provincial Hospital of Chinese Medicine, LanZhou, GanSu Province. P. R. China
Jin, WenMei
Not yet published in any medical journal. Collected in the special issue "Bu-Nao-Gao in the treatment of brain damage and children feeblemindedness" through internal distribution by the Provincial Hospital of Chinese Medicine, LanZhou, GanSu Province, P. R. China.

38. Clinical study of Bu-Nao-Gao in the treatment of paralysis resulting from head trauma (a trial of 66 cases).
Department of Cardiovascular and nervous system. Provincial Hospital of Chinese Medicine, LanZhou, GanSu Province. P. R. China
Xia, YongChao; Li, YianYi; Han, Yian; Xu, WenKe; Dou, YouYi; Zhu, YaPing; Zhang, MinSi; Lu, ShaoMin; Yang, YongShen; Hu, MinLi; Wu, QuanYen; Luo, Ling; Yian, XiaoXia;
Not yet published in any medical journal. Collected in the special issue "Bu-Nao-Gao in the treatment of brain damage and children feeblemindedness" through internal distribution by the Provincial Hospital of Chinese Medicine, LanZhou, GanSu Province, P. R. China.

39. Xia, YongChao; Li, YianYi; Han, Yian; Xu, WenKe; Dou, YouYi; Zhu, YaPing; Zhang, MinSi; Lu, ShaoMin;

Yang, YongShen; Wu, QuanYen; Hu, MinLi; Luo, Ling; Yian, XiaoXia. Clinical study of Bu-Nao-Gao in the treatment of 23 patients with motor neuron disease. Chinese Technology Journal of Chinese Medicine (Zhong Guo Zhong Yi Yiao Ke Ji). 1996, 3 (5): 43-.

Also collected in the special issue "Bu-Nao-Gao in the treatment of brain damage and children feeblemindedness" through internal distribution by the Provincial Hospital of Chinese Medicine, Lanzhou, GanSu Province, P. R. China.

40. Xia, YongChao et al., (case report prepared by Yang, YongShen). Illustration of typical cases of amyotrophic lateral sclerosis-ALS: Case #8.

Collected in the special issue "Bu-Nao-Gao in the treatment of brain damage and children feeblemindedness" through internal distribution by the Provincial Hospital of Chinese Medicine, LanZhou, GanSu Province, P. R. China.

Patient: 50 year-old female (Administration number #69834). Progressive upper limbs weakness for approximately 9 months, was admitted to the hospital on Sep. 18, 1992 with the diagnosis of amyotrophic lateral sclerosis (ALS). The patient begun feeling upper limb weakness without any known reason, later experienced difficulty of raising arms and were unable to unbutton her clothes, and also felt weakness on both lower limbs. EMG (done at other hospital): muscle abnormality of neuronal origin, all nerves tested showed abnormalities of different extents; Diagnosis by other hospital: amyotrophic lateral sclerosis (ALS); After failed all other regular treatments of both Chinese and Western Medicines, and with a progressively worsening condition, the patient was admitted to our hospital. Upon hospitalization: the patient showed weakness of all four limbs, could not raise her upper limbs above shoulder, both hand could not do gripping and stretching, could not unbutton her clothes, difficulty of lifting her feet while walking with a feeling of rigidity, could only go up and down stairs by holding onto railing, could see muscle jumping all over her body.

Tongue: pink red, with a thin white coat, fine pulse. Physical exam: Cranial nerves (normal); obvious atrophy of thenar muscles interosseous muscles and forearm muscles and fasciculation, and muscle strength III$^-$; no muscle atrophy in the lower limbs, and muscle strength III$^+$; muscle tone of four limbs (low); reflexs of ankel-jerk, Biceps-jerk, Triceps-jerk and Knee-jerk are all hyperactive; Unable to induce pathological reflexes. No abnormalities of bladder control and bowel movement; No abnormality in sensory. Diagnosis according to Western Medicine: amyotrophic lateral sclerosis (ALS). Diagnosis according to Chinese Medicine: Wei Zheng (belong to insufficiencies of liver and kidney, and insufficiencies of Qi and blood), therefore the treatment strategy require nourishment of liver, kidney, Qi and blood. Treatment given: Bu-Nao-Gao (two cubes/day) alone. Two weeks after Bu-Nao-Gao: increased muscle strength in four limbs, could raise upper limbs above head but could not stretch straight; reduced rigidity in the lower limbs and reduced muscle jumping in whole body. One month after Bu-Nao-Gao: could raise upper limbs above should and could stretch straight, could do up and down stairs more freely than before. Two months after Bu-Nao-Gao, all five fingers of both hands could stretch out and could unbutton clothes, could go up and down stairs easily, muscle strength III$^+$–V$^-$. After being considered to have made an notable improvement, the patient was discharged from the hospital.

41. Xia, YongChao et al, (case report prepared by Lu, ShaoMin). Illustration of typical cases of amyotrophic lateral sclerosis-ALS: Case #9.

Collected in the special issue "Bu-Nao-Gao in the treatment of brain damage and children feeblemindedness" through internal distribution by the Provincial Hospital of Chinese Medicine, LanZhou, GanSu Province, P. R. China.

Patient: 25 year-old male (Administration number #73819). Weakness of four limbs for approximately one year, was admitted to the hospital on Aug. 7, 1993 with the diagnosis of amyotrophic lateral sclerosis (ALS). Upon hospitalization: the patient showed weakness of all four limbs, weak gripping (only 5 Kg), obvious muscle atrophy of four limbs and both hands, twitching of both upper limbs, unsteady walking (could only manage 100 meters), difficulty of walking up and down stairs. Tongue: red, with white coat, fine pulse. Physical exam: Lung and heart (–), muscle strength of four limbs (grade III), muscle tone (normal), tendon reflex (hyperactive), Babinski sign on both sides (+), Hoffmann sign on both sides (+); EEG: injury of neuronal origin. Diagnosis according to Chinese Medicine: Wei Zheng (liver and kidney weakness); Diagnosis according to Western Medicine: amyotrophic lateral sclerosis (ALS). Treatment strategy: Bu-Nao-Gao (two cubes/day) alone. 20 days after Bu-Nao-Gao: slightly enriched muscle volume, walking more steadily than before, gripping of both hands increased from 5 Kg to 20 Kg, could walk by himself for 2–3 hours, could walk up and down stairs by himself rather easily, muscle strength of four limbs V-. After one-month treatment with Bu-Nao-Gao, significant improvement was observed and the patient was discharged.

42. Xia, YongChao. Bu-Nao-Gao in the treatment of two patients in vegatative states.

Collected in the special issue "Bu-Nao-Gao in the treatment of brain damage and children feeblemindedness" through internal distribution by the Provincial Hospital of Chinese Medicine, LanZhou, GanSu Province, P. R. China.

Patient #1: 18 year-old female, in a vegetative state for 10 months after initial head injury. After taking Bu-Nao-Gao (the cube form) for 10 days, she appeared to be in a slightly conscious state and to be able to recognize people; on the 15$^{th}$ day, she was able to swallow food and feeding tube was removed; on 20$^{th}$ day, she was able to speak simple words and could recognize her parents, had some improvement on limb muscle strength (strength grade I); Two months after Bu-Nao-Gao, she showed continued improvement on consciousness and intelligence (could remember her date of birth, could call out the names of her classmate, could tell Dr. Xia that "Uncle Xia, I have lost my mind", could translate a few English words into Chinese), etc (note: this is only a partial translation).

Patient #2: 17 year-old female, in a vegetative state for 6 month after brain surgery.

Diagnosis: Injury to cerebral and brain stem, coma, decerebral rigidity (vegetative state).

14 days after taking Bu-Nao-Gao, she appeared to be in a slightly conscious state and could recognize objects; 20 days after taking Bu-Nao-Gao, she could answer yes or no with her eyes and could express her emotions; 30 days after taking Bu-Nao-Gao, she regained complete consciousness, and her muscle strength had improved with decreased rigidity; 60 days after taking Bu-Nao-Gao, she could speak simple sentences; 70 days after taking Bu-Nao-Gao, she could sit up and turn her neck, her muscle strength in four limbs was I–III with reduced muscle rigidity, and her decerebrate rigidity was relieved.

(note: this is only a partial translation).

43. Xia, YongChao; Han, Yian; Zhang, MinShi and Li, YianYi. Bu-Nao-Gao for the treatment of Oliverpontocerebellar atrophy (Dejerine-Thomas type, 3 cases). China College Journal of Medicine (Zhong Guo Yi Yiao Xue Xue Bao) 1992, 6.

Also collected in the special issue "Bu-Nao-Gao in the treatment of brain damage and children feeblemindedness" through internal distribution by the Provincial Hospital of Chinese Medicine, LanZhou, GanSu Province, P. R. China.

44. Yang, YongSheng; Han, Yian; Xia, YongChao. Bu-Nao-Gao for the treatment of hereditary cerebellar ataxia (3 cases) Collection of the Second China Conference on Difficult and Complicated diseases, 1994: June at Bei-Dai-He.

Also collected in the special issue "Bu-Nao-Gao in the treatment of brain damage and children feeblemindedness" through internal distribution by the Provincial Hospital of Chinese Medicine, LanZhou, GanSu Province, P. R. China.

45. Li, YianYi; Xia, YongChao. Clinical cure of one patient with acute myelitis by Bu-Nao-Gao. Journal of GanSu College of Traditional Chinese Medicine (GanSu ZhongYi XueYuan XueBao). 1994, 11 (1), 31.

Patient: 37 year-old female, weakness of lower limbs and urine retention for 6 days. The patient had a cold two weeks prior the weakness. Bu-Nao-Gao (the cube/tar form, example 1 of the current application) was given at a 2-cubes/day dosage. On the 6th days of Bu-Nao-Gao treatment, urine retention was resolved, and urethal catheter was removed; On the 10th day after Bu-Nao-Gao, she could walk on flat ground with a cane; on $20^{th}$ day after Bu-Nao-Gao, she could walk freely with a normal gait, and could walk up and down stairs without aid, the muscle strength of four limbs reached grade V, but the painful sensation around waist somewhat remained. She continued to be on Bu-Nao-Gao for another two months, and clinical cure was achieved in this patient.

46. Xia, YongChao et al, One patient with sequel of toxic encephalopathy (five months). (case report prepared by Yang, YongSheng). Illustration of typical cases: Case #7 (Toxic encephalopathy).

Collected in the special issue "Bu-Nao-Gao in the treatment of brain damage and children feeblemindedness" through internal distribution by the Provincial Hospital of Chinese Medicine, LanZhou, GanSu Province, P. R. China.

Patient: 5-year-old boy (administration # 71928) Dementia, aphasia, could not stand or walk, very low intelligence (DQ=13). After hospitalization, he was treated with Bu-Nao-Gao (one cube/day). 10 days after treatment, he was able to walk with just a little assistance by others; 1 month later, he could walk by himself for 1–2 steps, could say "mum"; 2 month later, he could walk more steadily, and could walk for five meters on his own, muscle strength of both lower limbs IV$^+$. He was considered to have made a notable improvement and was discharged from the hospital.

47. Xia, YongChao; Li, YianYi. Treatment of giant cell arteritis. Hu-Nan Journal of Traditional Chinese Medicine. 1990, 3:32–33.

A self-designed "Fu-Shou-Yi-Qi-Huo-Xie" decoction was used for treating three patients with giant cell arteritis. The three patients were a 29-year old male with a 2-year history, a 20-year-old female and a 42-year old male. Clinical cure was achieved in all three patients after 20–60 day's treatment. After 1–3 year follow-up, no relapse was reported in all three patients.

The decoction reported here lacked one of the core ingredients in the currently applied formulation—"the Bu-Nao-Gao" formulation. And many components which were not used in "the Bu-Nao-Gao" formulation were also tested therefore made the consensus formulation not obvious.

What is claimed is:

1. A composition administered daily to a subject consisting essentially of Radix *angelica sinensis* (DangGui) 0.82 g–3.3 g/Kg body weight, *Ligusticum chuanxiong* (Chuanxiong) 0.1–1.2 g/Kg body weight, Hirudo (Shuizhi) 0.1–0.4 g/Kg body weight, *Polygonatum sibiricum* (HuangJing) 0.2–0.8 g/kg body weight wherein these dosages may increase up to 2.5 times if the body weight of the subject is less than 40 kg.

2. The composition of claim 1, wherein *Ligusticum chuanxiong* (Chuanxiong) is replaced by *Carthamus tinctorius* (Hong Hua) at the same daily dosage range 0.1–1.2 g/Kg body weight wherein these dosages may increase up to 2.5 times if the body weight of the subject is less than 40 kg.

3. A pharmaceutical composition for the treatment of head and spinal cord injuries comprising effective amount of the composition of claim 1 and a pharmaceutically acceptable carrier.

4. A pharmaceutical composition for the treatment of mental retardation and cerebral palsy comprising effective amount of the composition of claim 1 and a pharmaceutically acceptable carrier.

5. A pharmaceutical composition for the treatment of motor neuron disease comprising effective amount of the composition of claim 1 and a pharmaceutically acceptable carrier.

6. A pharmaceutical composition for the treatment of head and spinal cord injuries comprising effective amount of the composition of claim 2 and a pharmaceutically acceptable carrier.

7. A pharmaceutical composition for the treatment of mental retardation and cerebral palsy comprising effective amount of the composition of claim 2 and a pharmaceutically acceptable carrier.

8. A pharmaceutical composition for the treatment of motor neuron disease comprising effective amount of the composition of claim 2 and a pharmaceutically acceptable carrier.

9. A composition administered daily to a subject consisting essentially of Radix *angelica sinensis* (DangGui) 0.82 g–3.3 g/Kg body weight, *Ligusticum chuanxiong* (Chuanxiong) 01–1.2 g/Kg body weight, Hirudo (Shuizhi) 0.1–0.4 g/Kg body weight, *Polygonatum sibiricum* (HuangJing) 0.2–0.8 g/Kg body weight wherein these dosages may increase up to 2.5 times if the body weight of the subject is less than 40 kg, *Astragalus membranaceus* (HuangQi) 0.315 g–1.2 g/Kg body weight daily wherein these dosages may increase up to 2.5 times if the body weight of the subject is less than 40 kg.

10. The composition of claim 9, wherein *Ligusticum chuanxiong* (Chuanxiong) is replaced by *Carthamus tinctorius* (Hong Hua) at the same daily dosage range 0.1–1.2 g/Kg body weight wherein these dosages may increase up to 2.5 times if the body weight of the subject is less than 40 kg.

11. A composition administered daily to a subject consisting essentially of Radix *angelica sinensis* (DangGui) 0.82 g–3.3 g/Kg body weight, *Ligusticum chuanxiong* (Chuanxiong) 0.1–1.2 g/Kg body weight, Hirudo (ShuiZhi) 0.1–0.4 g/Kg body weight, *Polygonatum sibiricum* (HuangJing) 0.2–0.8 g/kg body weight wherein these dosages may increase up to 2.5 times if the body weight of the subject is less than 40 kg, *Glycyrrhiza uralensis* (Gancao) 0.06–0.21 g/Kg body weight wherein these dosages may increase up to 2.5 times if the body weight of the subject is less than 40 kg.

12. The composition of claim 11, wherein *Ligusticum chuanxiong* (Chuanxiong) is replaced by *Carthamus tinctorius* (Hong Hua) at the same daily dosage range 0.1–1.2 g/Kg body weight wherein these dosages may increase up to 2.5 times if the body weight of the subject is less than 40 kg.

13. A pharmaceutical composition for the treatment of head and spinal cord injuries comprising effective amount of the composition of claim 9 and a pharmaceutically acceptable carrier.

14. A pharmaceutical composition for the treatment of mental retardation and cerebral palsy comprising effective amount of the composition of claim 9 and a pharmaceutically acceptable carrier.

15. A pharmaceutical composition for the treatment of motor neuron disease comprising effective amount of the composition of claim 9 and a pharmaceutically acceptable carrier.

16. A pharmaceutical composition for the treatment of head and spinal cord injuries comprising effective amount of the composition of claim 11 and a pharmaceutically acceptable carrier.

17. A pharmaceutical composition for the treatment of mental retardation and cerebral palsy comprising effective amount of the composition of claim 11 and a pharmaceutically acceptable carrier.

18. A pharmaceutical composition for the treatment of motor neuron disease comprising effective amount of the composition of claim 11 and a pharmaceutically acceptable carrier.

* * * * *